(12) United States Patent
de Boer et al.

(10) Patent No.: US 11,744,708 B2
(45) Date of Patent: Sep. 5, 2023

(54) SURFACE TOPOGRAPHIES FOR ALTERING THE PHYSIOLOGY OF LIVING CELLS

(71) Applicant: KONINKLIJKE PHILIPS N.V., Eindhoven (NL)

(72) Inventors: Jan de Boer, Zeist (NL); Berendien Jacoba Papenburg, Terwolde (NL); Godefridus Franciscus Bernardus Hulshof, Nijmegen (NL)

(73) Assignee: Koninklijke Philips N.V., Eindhoven (NL)

( * ) Notice: Subject to any disclaimer, the term of this patent is extended or adjusted under 35 U.S.C. 154(b) by 326 days.

(21) Appl. No.: 15/998,578

(22) PCT Filed: Feb. 16, 2017

(86) PCT No.: PCT/NL2017/050092
§ 371 (c)(1),
(2) Date: Aug. 16, 2018

(87) PCT Pub. No.: WO2017/142405
PCT Pub. Date: Aug. 24, 2017

(65) Prior Publication Data
US 2020/0253738 A1    Aug. 13, 2020

(30) Foreign Application Priority Data
Feb. 16, 2016  (NL) ..................... 2016275
Oct. 28, 2016  (NL) ..................... 2017684

(51) Int. Cl.
*A61F 2/30* (2006.01)
*A61C 8/02* (2006.01)
(Continued)

(52) U.S. Cl.
CPC ........ *A61F 2/30771* (2013.01); *A61C 8/0006* (2013.01); *C12M 23/02* (2013.01);
(Continued)

(58) Field of Classification Search
CPC .......... A61C 8/0006; A61C 2008/0046; A61F 2/30771; A61F 2/20767;
(Continued)

(56) References Cited

U.S. PATENT DOCUMENTS 4,865,603 A * 9/1989 Noiles ................ A61F 2/30771
                                                    72/71
5,348,788 A * 9/1994 White ................... A61F 2/0077
                                                    428/131
(Continued)

FOREIGN PATENT DOCUMENTS

AU    2002302804 B2    5/2008
CN      104609029 A    5/2015
(Continued)

OTHER PUBLICATIONS

Abstract: Zeng G.H. et al. "Non-proteinaceous bacterial adhesins challenge the antifouling properties of polymer brush coatings". Acta Biomaterialia vol. 24 Issue:—Article No.—DOI: 10.1016/j.actbio.2015.05.037 Published: Sep. 15, 2015 p. 64-73.
(Continued)

*Primary Examiner* — Ralph A Lewis

(57) ABSTRACT

The invention pertains to surface topographies which can be used to modulate the morphology, proliferation, biochemical functioning, differentiation, attachment, migration, signaling, and/or cell death of a cell population by physical stimulation. Such topographies can be applied in vitro and in vivo to modulate cell behavior. Specific examples include implants provided with a topography of the invention which regulates the immune response, or an implant which increases osteogenesis. The invention furthermore pertains to objects which are used in vitro to modulate cell behavior.

17 Claims, 16 Drawing Sheets

(51) Int. Cl.
*C12M 1/00* (2006.01)
*A61C 8/00* (2006.01)

(52) U.S. Cl.
CPC ............... *A61C 2008/0046* (2013.01); *A61F 2002/3093* (2013.01); *A61F 2002/30838* (2013.01); *A61F 2002/30891* (2013.01); *A61F 2310/00011* (2013.01); *A61F 2310/00179* (2013.01)

(58) Field of Classification Search
CPC .... A61F 2002/30891; A61F 2002/3093; A61F 2002/3084; A61F 2002/30838
See application file for complete search history.

(56) References Cited

U.S. PATENT DOCUMENTS

| | | | |
|---|---|---|---|
| 6,419,491 B1* | 7/2002 | Ricci | A61C 8/0012 433/173 |
| 7,143,709 B2 | 12/2006 | Brennan et al. | |
| 8,574,704 B2 | 11/2013 | Smith et al. | |
| 8,808,724 B2 | 8/2014 | Cichocki et al. | |
| 9,016,221 B2 | 4/2015 | Brennan et al. | |
| 2001/0039454 A1* | 11/2001 | Ricci | A61F 2/32 623/23.5 |
| 2005/0119758 A1* | 6/2005 | Alexander | A61F 2/30771 623/23.5 |
| 2011/0086427 A1* | 4/2011 | Faris | C12M 29/10 435/395 |
| 2012/0312778 A1* | 12/2012 | Ullrich, Jr. | C23C 14/34 451/28 |
| 2013/0110255 A1* | 5/2013 | Picha | A61L 27/50 623/23.74 |
| 2013/0199539 A1 | 8/2013 | Webster | |
| 2020/0306015 A1* | 10/2020 | Su | A61C 8/0022 |

FOREIGN PATENT DOCUMENTS

| | | |
|---|---|---|
| EP | 1095760 A1 | 5/2001 |
| JP | 2007-525280 A | 9/2007 |
| JP | 2008106398 A | 5/2008 |
| JP | 2013-507922 A | 3/2013 |
| WO | 2003013827 A1 | 2/2003 |
| WO | 2006/022878 A1 | 3/2006 |
| WO | 2008070625 A2 | 6/2008 |
| WO | 2011/046884 A2 | 4/2011 |
| WO | 2011094344 A1 | 8/2011 |
| WO | 2012058605 A1 | 5/2012 |
| WO | 2013003373 A1 | 1/2013 |
| WO | 2015038916 A2 | 3/2015 |

OTHER PUBLICATIONS

Abstract: Pegalajar-Jurado, A. et al. "Fabrication of a platform to isolate the influences of surface nanotopography from chemistry on bacterial attachment and growth". Biointerphases vol. 10 Issue: 1 Article No. 011002 DOI: 10.1116/1.4913377 Published: Mar. 2015.
Abstract: Halder, P. et al. "An assessment of the dynamic stability of microorganisms on patterned surfaces in relation to biofouling control" Biofouling vol. 30 Issue: 6 Article No. DOI: 10.1080/08927014.2014.914177Published: 2014 p. 695-707.
Abstract: Vasudevan R.et al. "Microscale patterned surfaces reduce bacterial fouling-microscopic and theoretical analysis". Colloids and Surfaces B-Biointerfaces vol. 117 Issue:—Article No.—DOI: 10.1016/j.colsurfb.2014.02.037 Published: May 1, 2014 p. 225-232.
Abstract: Graham M.V. et al. "Development of antifouling surfaces to reduce bacterial attachment" Soft Matter vol. 9 Issue: 27 Article No.—DOI: 10.1039/c3sm50584g Published: 2013 p. 6235-6244.
Abstract: Nill P. et al. "Influence of surface patterning on bacterial growth behavior". Journal of Vacuum Science & Technology B vol. 29 Issue: 6 Article No. 06FA03 DOI: 10.1116/1.3662084 Published: Nov. 2011.
Abstract: Bazaka K. et al. "Do bacteria differentiate between degrees of nanoscale surface roughness?"; Biotechnology Journal vol. 6 Issue: 9 Article No.—DOI: 10.1002/biot.201100027 Published: Sep. 2011 p. 1103-1114.
Abstract: D'Souza F. et al. "Bacterial assay for the rapid assessment of antifouling and fouling release properties of coatings and materials" Journal of Industrial Microbiology & Biotechnology vol. 37 Issue: 4 Article No.—DOI: 10.1007/s10295-009-0681-1 Published: Apr. 2010 p. 363-370.

\* cited by examiner a

Ti implant featuring surface topography →

Bone tissue growthing towards the implant → b

Ti implant featuring surface topography →

Bone tissue growthing towards the implant →

Table 1

| Protrusion number | Protrusion shape | Distance between protrusions (μm) (equaling valley width) | | | Surface area coverage by protrusions (%) | Protrusion top surface area (μm²) | performance | |
| | | Shortest | Longest | Mean | | | Number of attached cells | Surface coverage by cells (%) |
|---|---|---|---|---|---|---|---|---|
| E1 |  | 3 | 28 | 17 | 11 | 88 | 60 | 35 |
| E2 |  | 6 | 28 | 17 | 25 | 196 | 49 | 32 |
| E3 |  | 4 | 28 | 17 | 28 | 221 | 53 | 35 |
| E4 |  | 4 | 20 | 13 | 23 | 91 | 56 | 35 |
| E5 |  | 2 | 16 | 8 | 29 | 29 | 50 | 29 |
| E6 |  | 3 | 28 | 19 | 19 | 147 | 52 | 31 |
| E7 |  | 7 | 20 | 13 | 35 | 101 | 55 | 35 |
| E8 |  | 2 | 28 | 15 | 14 | 105 | 49 | 31 |
| E9 |  | 3 | 28 | 11 | 29 | 221 | 47 | 29 |
| E10 |  | 6 | 20 | 11 | 28 | 104 | 44 | 31 |
| EP |  | . | . | . | . | . | 44 | 27 |
| B1 |  | 3 | 18 | 8 | 36 | 29 | 73 | 35 |
| B2 |  | 3 | 20 | 14 | 7 | 145 | 85 | 23 |

Figure 15

| Protrusion number | Protrusion shape | Distance between protrusions (μm) (equaling valley width) | | | Surface area coverage by protrusions (%) | Protrusion top surface area (μm²) | performance | |
|---|---|---|---|---|---|---|---|---|
| | | Shortest | Longest | Mean | | | Integrated ALP intensity (iALP, a.u.) | Relative integrated ALP intensity (riALP, a.u.) |
| O1 |  | 1 | 20 | 8 | 56 | 335 | 648 | 58 |
| O2 |  | 4 | 31 | 15 | 43 | 383 | 1034 | 43 |
| O3 |  | 5 | 30 | 16 | 40 | 329 | 834 | 48 |
| O4 |  | 7 | 39 | 17 | 38 | 311 | 946 | 39 |
| O5 |  | 2 | 11 | 5 | 48 | 48 | 719 | 56 |
| O6 |  | 2 | 31 | 11 | 35 | 183 | 852 | 52 |
| O7 |  | 3 | 17 | 9 | 54 | 433 | 718 | 51 |
| O8 |  | 1 | 30 | 16 | 45 | 362 | 597 | 49 |
| O9 |  | 6 | 27 | 12 | 58 | 480 | 637 | 58 |
| O10 |  | 1 | 11 | 5 | 37 | 38 | 944 | 36 |

| Protrusion number | Protrusion shape | Distance between protrusions (μm) (equaling valley width) | | | Surface area coverage by protrusions (%) | Protrusion top surface area (μm²) | performance | |
|---|---|---|---|---|---|---|---|---|
| | | Shortest | Longest | Mean | | | Integrated ALP intensity (iALP, a.u.) | Relative integrated ALP intensity (riALP, a.u.) |
| NP |  | - | - | - | - | - | 212 | 14 |
| B3 |  | 2 | 18 | 10 | 8 | 30 | 329 | 19 |
| B4 |  | 7 | 25 | 22 | 4 | 28 | 345 | 14 |
| B5 |  | 2 | 9 | 7 | 25 | 25 | 513 | 17 |

Figure 16

| Protrusion number | Protrusion shape | Distance between protrusions (μm) (equaling valley width) | | | Surface area coverage by protrusions (%) | Protrusion top surface area (μm²) | performance | |
| --- | --- | --- | --- | --- | --- | --- | --- | --- |
| | | Shortest | Longest | Mean | | | Mean number of macrophages attached | Multi-nucleation (x,y) |
| I1 (XXL) | | 3 | 20 | 13 | 7 | 29 | 12 | 13 |
| I2 (XXL) | | 6.5 | 20 | 11 | 17 | 67 | 14 | 14 |
| I3 (XXL) | | 4 | 38 | 19 | 8 | 80 | 14 | 12 |
| I4 (S-X) | | 4 | 19 | 8 | 21 | 21 | 15 | 18 |
| I5 (L/L) | | 1 | 18 | 7 | 48 | 181 | 4 | 5 |
| I6 (L/L) | | 1 | 19 | 5 | 47 | 47 | 3 | 4 |
| I7 (L/L) | | 2 | 29 | 16 | 48 | 192 | 4 | 4 |
| I8 (L/L) | | 2 | 19 | 6 | 40 | 40 | 3 | 4 |
| I9 (L/L) | | 0.5 | 19 | 3 | 45 | 45 | 5 | 5 |
| I10 (L/L) | | 2 | 19 | 5 | 45 | 45 | 4 | 4 |

| Protrusion number | Protrusion shape | Distance between protrusions (μm) (equaling valley width) | | | Surface area coverage by protrusions (%) | Protrusion top surface area (μm²) | performance | |
| --- | --- | --- | --- | --- | --- | --- | --- | --- |
| | | Shortest | Longest | Mean | | | Mean number of macrophages attached | Multi-nucleation (x,y) |
| I11 (L/L) | | 1 | 19 | 6 | 27 | 27 | 4 | 4 |
| I12 (L/L) | | 5 | 29 | 9 | 44 | 177 | 4 | 4 |
| I13 (L/L) | | 2 | 19 | 5 | 34 | 34 | 5 | 4 |
| 20P | | . | . | . | . | . | 6 | 6 |
| S6 | | 2 | 7 | 5 | 19 | 19 | 10 | 10 |
| S7 | | 5 | 27 | 16 | 18 | 104 | 8 | 7 |

SURFACE TOPOGRAPHIES FOR ALTERING THE PHYSIOLOGY OF LIVING CELLS

RELATED APPLICATION DATA

This application is a National Stage Application under 35 U.S.C. 371 of PCT application PCT/NL2017/050092 designating the United States and filed Feb. 16, 2017; which claims the benefit of NL application number 2017684 and filed Oct. 28, 2016; and NL application number 2016275 and filed Feb. 16, 2016 each of which are hereby incorporated by reference in their entireties.

INTRODUCTION

The invention pertains to surface topographies which have been found to modulate the physiological state of cells such as, but not limited to, morphology, proliferation, biochemical functioning, differentiation, attachment, migration, signaling, and/or cell death of a cell population by physical stimulation. The invention furthermore pertains to objects, provided with at least one such topography, which can be used in vivo or in vitro to alter cell behavior, as well as to methods to alter cell behavior using such objects.

It is known that cells can contact and interact with a surface. In nature, the direct physical interaction between cells and their environment is part of their normal physiological behavior. When cells are cultured out of their natural environment, for instance in a cell culture dish, or when cells are exposed to non-natural environments, such as is the case when exposed to medical implants such as hip implants or pacemakers, their physiology is typically not the same as in their original environment. Many efforts are put into optimizing these cellular responses in vitro and on implant surfaces.

In cell cultures, for example, cells can be placed on a surface while in a suitable culture medium, the goal being to have these cells to proliferate as naturally as possible, and/or express specific biological properties such as differentiation, and/or responding to a specific chemical, physical or electrical stimulus. A conventional strategy to change cell behavior is to add a variety of hormones, chemical compounds, growth factors, enzymes, salts and the like, which may have the effect of an altered cell response, such as a change in proliferation or an induced differentiation. However, although such changes can be achieved on a surface, altered cell behavior in these conventional cultures is generally chemically induced, through interaction of the hormones, chemical compounds, growth factors, enzymes, salts and the like with the cell surface and/or cell interior. In such conventional cultures as well as on medical implants, potential micropatterns present on the surface generally are not taken into account.

It has recently been found that physical interaction affects cell behavior. For example, it has been shown that titanium-based implants featuring surface micro-roughness caused by chemical etching and/or mechanical blasting improves the mechanical strength of newly-formed tissues bridging the implant to the bone/dental tissue [Buser D et al. Int J Oral Maxillofac Implants 1998; 13(5):611-619., Buser D et al. J Biomed Mater Res 1999; 45(2):75-83.].

The impact of topographical cues at cell level has been observed in different cell types. For example, it is shown that hepatocyte cell attachment, morphology and function were remarkably improved when cultured on surfaces featuring nano-topographies as compared to smooth substrates [You J et al. ACS Appl. Mater. Interfaces 2015; 5:12299-12308.].

DESCRIPTION OF FIGURES

FIG. 15 illustrates unit cell and protrusion design parameters and performance of topographies to stimulate osteogenesis. Protrusion shape: white indicates the top surface area, black indicates the valley surface. Geometrical parameters are based on calculations. Nonpatterned (NP) sample and a selection of 'basic topographies' (circles, triangles and rectangles) are included as controls.

FIG. 16 illustrates unit cell and protrusion design parameters and performance of topographies for immunoregulation. Protrusion shape: white indicates the top surface area, black indicates the valley surface. Geometrical parameters are based on calculations. Nonpatterned (NP) sample and a selection of 'basic topographies' (circles, triangles and rectangles) are included as controls.

DETAILED DESCRIPTION

Figure 1:
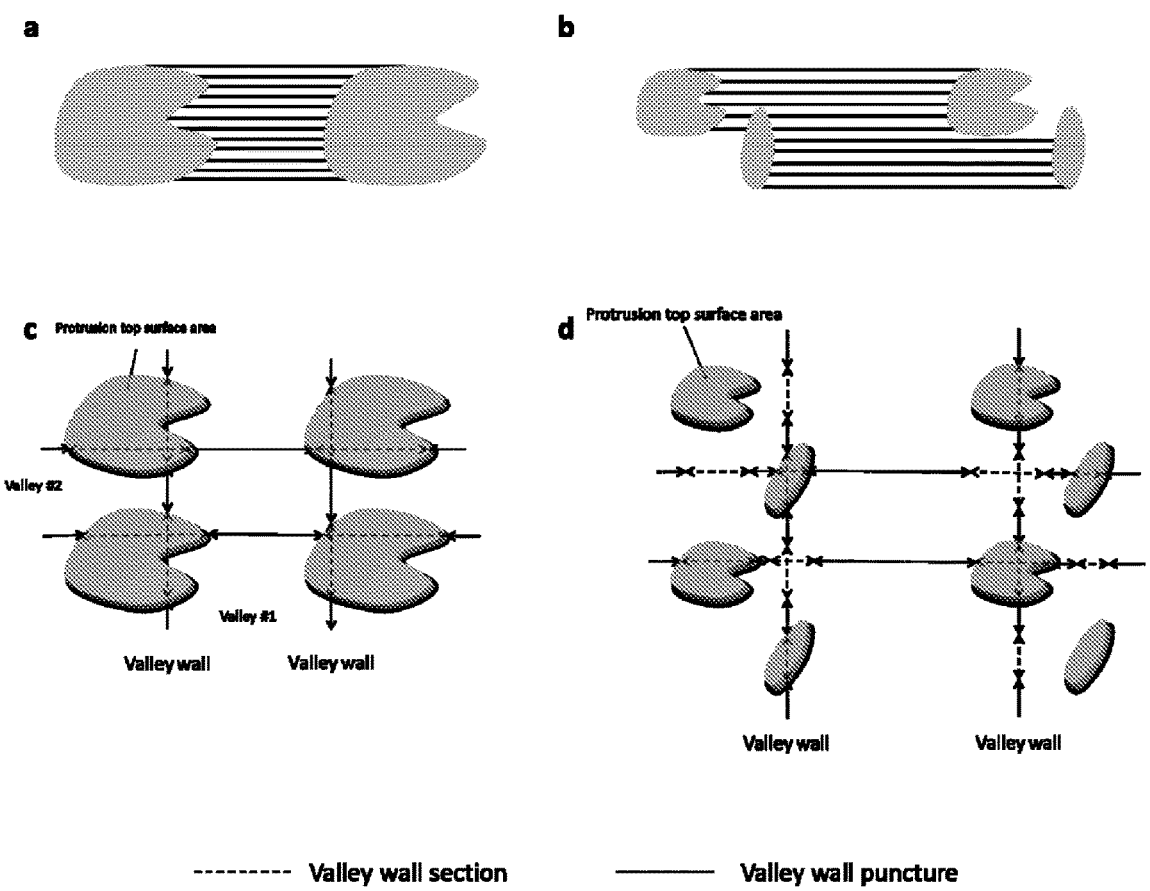
FIG. 1a, b: Schematic top view of two adjacent protrusions comprising (a) one and (b) two protrusion elements. (Imaginary) sample lines indicate the method used for determining the average distance between the two adjacent protrusions.
FIG. 1c, d: 3D schematic top view of 2×2 pattern of protrusions, containing (c) one and (d) two protrusion elements. Protrusions, valley walls, valley wall sections and valley wall punctures are indicated.

Generic Embodiments: Topographies for Modulating Cell Response

The invention pertains to a surface topography, as well as to an object comprising a surface part provided with one or more of such topographies. The surface topography is formed by the presence of regularly spaced protrusions on the surface part, and can be defined by two alternative definitions. In one definition, the surface topography can be defined by the average distance between adjacent protrusions, the top surface area of the protrusions, and the coverage of the surface part, and furthermore by the length and width of the protrusions (the "protrusion"-definition). In another definition, the topography can be defined by the valleys which are located between the protrusions (the "valley"-definition). These definitions function as two alternative numerical representations of a topography.

The "Protrusion" Definition

The present invention provides an object, comprising a surface part provided with one or more topographies capable of modulating the morphology, proliferation, biochemical functioning, differentiation, attachment, migration, signaling, and/or cell death of a cell population by physical stimulation, and wherein the topography comprises a surface provided with a regular pattern of protrusions, which protrusions comprise one or more protrusion elements, which protrusion elements are defined as surface portions elevated above the surface having a top surface area and a circumferential side face connecting the top surface area with the surface, wherein each protrusion element has a maximum height of between 0.5 and 50 μm above the surface, and wherein
  a) the average distance between adjacent protrusions is between 0 and 50 μm;
  b) the top surface area of the protrusion is between 1 and 6000 μm$^2$; and
  c) the protrusions cover between 3 and 90% of the surface.

Preferably, the object of the invention has a length and width of the protrusions or protrusion elements as follows:
  a) if the protrusion comprises one protrusion element:
  the length of the protrusion, defined as the length of the longest straight-line fitting within the circumference of the top surface area parallel to the surface, is 0.01-100 μm;
  the width of the protrusion, defined as the length of the longest straight-line fitting within the circumference of the top surface area parallel to the surface, perpendicular to the length, is 0.01-100 μm;
  b) if the protrusion comprises more than one protrusion element: the length of each protrusion element, defined as the length of the longest straight-line fitting within the circumference of the top surface area parallel to the surface, is 0.01-100 μm;
  the width of each protrusion element, defined as the length of the longest straight-line fitting within the circumference of the top surface area parallel to the surface perpendicular to the length, is 0.01-100 μm;
  the average distance between two circumferences of adjacent protrusion elements of the same protrusion is 0-50 μm.

The topography comprises a surface provided with a regular pattern of protrusions. Protrusions are comprised of one or more protrusion elements, which elements are surface portions elevated above the surface on which the protrusions are formed, i.e. a surface surrounding the relevant protrusion or protrusion element. Each protrusion element is defined by an elevated surface portion and by a top surface area, as well as by a circumferential side face which connects the top surface area with the surface. The elevated surface portion is the total of the top surface area and the circumferential side face. One protrusion may be defined as a single protrusion element, but one protrusion may also comprise multiple protrusion elements. In one preferred embodiment, a protrusion comprises a single protrusion element. In another preferred embodiment, a protrusion comprises at least two protrusion elements.

As such, protrusions are small bumps or groups of bumps on the surface. The protrusions define between them a three-dimensional network of valleys in the surface of the object. It has been found that a regular pattern of protrusions with a specific size, shape and configuration results in a topography that is capable of modulating the cell response, most notably morphology, proliferation, biochemical functioning, differentiation, attachment, migration, signaling, and/or cell death of a cell population by physical stimulation.

The regular pattern can be defined by a grid of intersecting gridlines which can be laid over the surface, which gridlines define a pattern of unit cells, such that each unit cell comprises a maximum of one protrusion. Because the grid of intersecting gridlines need not physically be present, but preferably is an imaginary way to define the regular pattern, the unit cells may have any shape. Preferably, a unit cell has a rectangular, especially square, trapezoid, triangular or hexagonal shape.

A regular pattern in this context means that any section of the topography which consists of m unit cells, for instance in a m×n arrangement, is repetitively present in sections adjacent to that section. Preferably, m and n are 1, but m may be 4-16 and n may be 2-4, in particular in case of unit cells comprising differently shaped or differently oriented protrusions, or in case of triangular, hexagonal or trapezoid unit cells.

A unit cell may for instance have a surface area of between 1 and 10000 $\mu m^2$, preferably between 1 and 2500 $\mu m^2$, more preferably between 25 and 2000 $\mu m^2$, more preferably between 100 and 1000 $\mu m^2$. In case of square or rectangular unit cells, the unit cell may have length×width dimensions of (1-100) $\mu m$×(1-100) $\mu m$, preferably (1-50) $\mu m$×(1-50) $\mu m$. In highly preferred embodiments, unit cells are square and have length×width dimensions of 5 $\mu m$×5 $\mu m$ to 45×45 $\mu m$, preferably 5×5 to 30 $\mu m$×30 $\mu m$ such as for example 5 $\mu m$×5 $\mu m$, 10 $\mu m$×10 $\mu m$, 15 $\mu m$×15 $\mu m$, 20 $\mu m$×20 $\mu m$, 25 $\mu m$×25 $\mu m$ or 28 $\mu m$×28 $\mu m$.

The unit cells defined by the pattern of intersecting gridlines each comprise a maximum of a single protrusion, which protrusion may be comprised of multiple protrusion elements as defined above. Preferably, each unit cell comprises a protrusion of equal dimensions, i.e. each unit cell comprises protrusions identical to one another. The dimensions of a protrusion are defined as the total characterizing features, including for instance the height of the protrusion, the number and relative position of protrusion elements inside the unit cell, the length and width of each protrusion element, the angle of the circumferential side face relative to the surface, and the shape of the top surface area of each protrusion element.

The height of a protrusion, or at least of a protrusion element, is between 0.5 and 50 $\mu m$ above the surface. That is, the height of each protrusion element may be between 0.5 and 50 $\mu m$ above the surface, even though in case a protrusion comprises multiple protrusion elements, the height of various protrusion elements in the protrusion may be different within the mentioned boundaries. Preferably, however, the height of each protrusion element is the same. The height is measured as a maximum height of the top surface area of a protrusion or protrusion element above the surface, especially above a surrounding surface area within a unit cell.

Further preferably, the height of a protrusion may be between 1 and 45 $\mu m$, preferably between 2 and 40 $\mu m$, more preferably between 3 and 35 more preferably between 4 and 30 $\mu m$, even more preferably between 5 and 28 $\mu m$, even more preferably between 6 and 28 $\mu m$.

The number and relative position of protrusion elements inside a unit cell may vary from one unit cell to another as long as a regular pattern of protrusions is obtained. That is, two or more different unit cells comprising the same or different protrusions may be defined, which unit cells are placed in a regular pattern, for example alternate regularly on the surface. In case of triangular or trapezoid unit cells with protrusions of equal dimensions, this may result in a regular pattern of the same protrusions which have different orientations, for example alternatingly opposite orientation on the surface. In case of two different square unit cells each having a single, but different protrusion, an alternating pattern of said unit cells results in a regular pattern of rows of said protrusions, which rows are either oriented parallel to the edges of the unit cells, or parallel to the diagonal of the unit cell. Alternatively, square unit cells all having the same protrusion may be oriented differently on the surface, so as to obtain a surface in which the protrusions are regularly distributed with varying orientation.

Countless ways of obtaining a regular pattern of protrusions by applying the concept of unit cells may be devised, and can be used in the present invention. Preferably however, square, rectangular and hexagonal unit cells are all oriented in the same direction, while triangular unit cells are alternatingly oriented. Further preferably, all unit cells contain an identical protrusion.

The length of each protrusion (or in case of protrusions comprising multiple protrusion elements, the length of each protrusion element), is defined as the length of the longest straight-line fitting within a circumference of the top surface area of the protrusion or protrusion element, parallel to the surface.

In case of protrusions comprising only a single protrusion element, the length of a protrusion is 0.01-100 $\mu m$. Preferably, the length is 0.5-50 $\mu m$, more preferably 1-40 $\mu m$.

In case of protrusions comprising multiple protrusion elements, the length of a protrusion element is 0.01-100 $\mu m$. Preferably, the length is 0.1-45 $\mu m$, more preferably 0.5-40 $\mu m$, even more preferably 1-30 $\mu m$.

The width of each protrusion (or in case of protrusions comprising multiple protrusion elements, the width of each protrusion element), is defined as the length of the longest straight-line fitting within the circumference of the top surface area of the protrusion or protrusion element parallel to the surface, perpendicular to the length.

In case of protrusions comprising only a single protrusion element, the width of a protrusion is 0.01-100 $\mu m$. Preferably, the width is 0.5-50 $\mu m$, more preferably 1-40 $\mu m$ In case of protrusions comprising multiple protrusion elements, the width of a protrusion element is 0.01-100 $\mu m$. Preferably, the width is 0.1-45 $\mu m$, more preferably 0.5-40 $\mu m$, even more preferably 1-30 $\mu m$.

Furthermore, in case of protrusions comprising multiple protrusion elements, the number and relative position of protrusion elements inside the unit cell is an important feature of the dimensions of the protrusion.

The average distance between adjacent protrusion elements of the same protrusion is determined by dividing the sides of the protrusion elements which face each other into equal line segments of about 0.4 $\mu m$, and determining the distance of each line segment of the first protrusion element to the facing line segment of the adjacent protrusion element (see figure). The average of all distances is the average distance between the protrusion elements. Of course, when a protrusion comprises more than two protrusion elements, the average distance of one protrusion element to a second protrusion element of the same protrusion may be different from the average distance of the same protrusion element to a third protrusion element of the same protrusion. In case the angle between the surface and the circumferential side face of the protrusion element is not 90°, the average distance between adjacent protrusions is determined at half the height of the protrusion. The same type of calculation is applied for determining the average distance between two facing protrusions, as has been exemplified in FIG. 1*a* and 1*b*. "Facing" in this context means that the distance between adjacent protrusions is determined on the basis of line segments stretching between those protrusions, over the length of the protrusion which is the shortest.

Generally, the average distance between two protrusions is 0-50 µm, preferably 0.5-40 µm, even more preferably 1-30 µm, even more preferably 2-25 µm. The average distance between two protrusion elements in the same protrusion is similarly defined. In a much preferred embodiment, if the average distance between two adjacent protrusions in one direction is 0, then the average distance between adjacent protrusions in the direction perpendicular to that distance should be larger than 0. In an even more preferred embodiment, the average distance between adjacent protrusions in any direction is larger than 0.

Also, the surface topography can be defined by determining the shortest and the longest distance between facing protrusions. The shortest distance is defined by the shortest straight line as defined above for the calculation of average distance which can be drawn between two adjacent protrusions or protrusion elements. The shortest distance is preferably 0-50 µm, more preferably 0-40 µm, more preferably 0-20 µm, and more preferably 0-10 µm. In further preferred embodiments, the shortest distance is 1-50 µm, preferably 2-40 µm, more preferably 3-30 µm, even more preferably 4-20 µm The longest distance is defined as the longest straight line as defined above for the calculation of average distance which can be drawn between two adjacent protrusions or protrusion elements. The longest distance can be 0-50 µm, preferably 0.5-40 µm, more preferably 1-35 µm. In further preferred embodiments, the longest distance is 2-50 µm, preferably 3-40 µm, more preferably 4-30 µm, even more preferably 5-20 µm.

The circumferential side face of the protrusion elements may have any angle between 0 and 180° with the surface at the position where the side face intersects with the surface. An angle of 90° is defined as normal to the surface, and an angle between 0° and 90° is defined as the situation where the top surface area is larger than the elevated portion of the surface, so that the top surface area at least partially covers the surface. An angle between 90° and 180° is defined as the situation wherein the top surface area is smaller than the elevated portion of the surface. The elevated portion of the surface is defined as the circumference of the protrusion at the point where it intersects the surface. As such, angles between 0° and 90° lead to protrusion elements which have a top surface area which hangs over the surface, whereas angles between 90° and 180° lead to protrusion elements which rise gradually toward the top surface area.

Preferably, the circumferential side face of at least a portion of the protrusion or protrusion elements, preferably the whole protrusion or protrusion element, has an angle between 45° and 135° with the surface, more preferably between 60° and 120°, even more preferably between 75° and 115°, and even more preferably between 80° and 100°. Most preferably, the circumferential side face of at least a portion of the protrusion or protrusion elements, preferably the whole protrusion or protrusion element, extends substantially normal to the surface at the position where the side face intersects with the surface, such as at an angle of 88-92°. In a further preferred embodiment, all protrusion elements have about the same angle with the surface at the position where the side face intersects with the surface.

The shape of the top surface area of each protrusion element is also an important feature of the dimensions of the protrusion, and may also be referred to as the shape of the protrusion (or protrusion element). This is because this shape defines the shape of the valley walls where cells of adjacent tissue may grow to provide fixation. The shape of the circumference of the top surface area is determined parallel to the surface. As such, it is a top-view of the protrusion element, which may have any geometrical form. In some embodiments, the shape may comprise a circular, oval, triangular, square, rectangular, trapezoid, pentagonal, hexagonal, heptagonal or octagonal shape. Such generally known shapes will be referred to as basic shapes herein. In further embodiments, the shape may comprise a combination of basic shapes.

In some embodiments, the shape of the top surface area of each protrusion/protrusion element may not be a single geometric shape, such as a square, triangle, circle, octagonal, 5-pointed star, hexagonal, 3-pointed star, half moon, or a circle with a corner taken out ("pacman"). In some embodiments the shape may not be circular, oval, or a shape such as a polygon, triangle, rectangle, square, hexagon, star, parallelogram.

Figure 13:
FIG. 13 illustrates a chart showing shapes of protrusions.

In some embodiments, protrusions may have a shape as shown in FIG. 13. In other embodiments, the topography does not comprise a protrusion shaped as shown in FIG. 13. In one embodiment, a topography does not have shape 1 from FIG. 13. In another embodiment, a topography does not have shape 2 from FIG. 13. In another embodiment, a topography does not have shape 3 from FIG. 13. In yet other embodiments, a topography does not have, independently, shape 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 from FIG. 13. In some embodiments, the topography does not comprise a selection of the topographies in FIG. 13, and in further embodiments, the topography does not comprise all of the shapes in FIG. 13. In a preferred embodiment, the top surface area is a surface positioned substantially parallel to the surface, although the top surface area may be slightly concave or convex, such as for instance slightly dome-shaped.

Particularly preferred protrusions (or protrusion elements) comprise overlapping or adjacent combinations of basic shapes, preferably interconnected by one or more bridging or overlapping portions, so as to obtain a complex shape. It has been found that the effect of modulating the cell response, most notably morphology, proliferation, biochemical functioning, differentiation, attachment, migration, signaling, and/or cell death of a cell population by physical stimulation by protrusions with specifically defined complex shapes is influenced not only by the dimensions of the protrusion, but also by the shape of the protrusion (or protrusion elements) alone. For protrusions of similar height, weight, length and width, but of different shape, there is a distinct effect on the cell response of the physically stimulating surface part. The individual effect of the shape of protrusions on modulating morphology, proliferation, biochemical functioning, differentiation, attachment, migration, signaling, and/or cell death of a cell population by physical stimulation will be further elaborated upon in the examples.

In case the protrusion (or protrusion element) comprises a combination of basic shapes, a complex shape can be obtained. Complex shapes may comprise overlapping or adjacent circular, oval, triangular, square, rectangular, trapezoid, pentagonal, hexagonal, heptagonal or octagonal shapes. In case of adjacent basic shapes, the adjacent basic shapes are preferably connected by an overlapping (bridging) portion, so that the top-view of the basic shape has a larger surface area than the surface area of the basic shapes alone. The increased surface area relative to the separate shapes is preferably located between the basic shapes, effectively increasing the width of any point of contact between the basic shapes.

Further preferably, the circumferential side face of a protrusion (or protrusion element) is a continuous side face, which may be a connected series of straight line portions, connected by angles. Alternatively, the straight line segments and/or the angles can be smoothly curved, so as to obtain a smoothly curved circumferential side face.

A smoothly curved circumferential side face in this context means that the circumferential side face only has rounded corners. Corners may stem from their presence in a shape, such as the corners in squares, triangles and hexagons, but such corners may also stem from the contact point between two adjacent shapes in a protrusion element, or from the presence of an overlapping (or bridging) portion between two basic shapes in a protrusion element. That is, corners in this sense refers to corners when the protrusion is seen with a top-view. When all corners in the circumferential side face of a protrusion element are rounded, a smoothly curved circumferential side face is obtained.

In preferred embodiments, a protrusion has a complex shape. A complex shape is a combination of basic shapes, in which the basic shapes are present as single protrusion elements, or as overlapping or adjacent basic shapes. A complex shape is further defined by the amount of corners in the circumferential side face. A corner, in this respect, may be a straight or rounded corner, and can be defined as any change in direction in the circumferential side face (top-view). Corners which take the shape of a line with a length of 5% of the length of the circumferential side face will be dubbed a "bent". Straight lines in the circumferential side face will be called "straights".

A corner can be narrow or wide. Narrow corners are corners with an angle of less than 90°. That is, narrow corners result in a "spike" in the shape, which spike is either directed inward or outward, relative to the protrusion. Wide corners are corners in which protrusion's circumferential side face displays an angle of more than 90°. Straight corners are corners with an angle of 90°.

Complex shapes are defined as shapes having at least one wide corner, wherein preferably, the quantity of narrow corners is not the same as the quantity of wide corners. Alternatively, complex shapes comprise at least one bent (preferably at least two or at least three), and at least one corner (preferably at least two, more preferably at least three corners). In further alternative preferred embodiments, complex shapes comprise both at least one bent and at least one straight. In further preferred embodiments, a complex shape is a shape comprising more than two straights, preferably more than three, more preferably more than four, in which at least 75% (preferably at least 85%, more preferably at least 95%) of all straights are of different length. In other preferred embodiments, complex shapes comprise at least 3 bents.

An adjacent (or facing) protrusion to a protrusion in a particular unit cell is a protrusion which is present in a unit cell which shares a side with that particular unit cell. Adjacent unit cells are similarly defined. Unit cells which only share a corner with the particular unit cell are not adjacent. Given a regular pattern of protrusions, one protrusion is for example adjacent to three protrusions in case of triangular unit cells, to four protrusions in case of trapezoid, square or rectangular unit cells, and to six protrusions in case of hexagonal unit cells.

The top surface area of the protrusion is defined as the surface area of the protrusion at its most elevated circumference. It follows from the above that if a protrusion comprises multiple protrusion elements, that the top surface area of the protrusion is the sum of all surface areas of all protrusion elements of the protrusion, each determined at the most elevated circumference of the protrusion element. The top surface area of a protrusion may be determined by for instance counting the number of pixels (as 0.4 µm×0.4 µm elements) which make up the top surface area of the protrusion (or protrusion element).

The top surface area of the protrusion is between 1 and 6000 µm$^2$, preferably 10 and 3000 µm$^2$, more preferably between 20 and 1500 µm$^2$, more preferably between 25 and 1000 µm$^2$, even more preferably between 30 and 750 µm$^2$.

The coverage of the protrusions is defined as the percentage of top surface area relative to the full area which is covered by protrusions. Thus, the coverage is the sum of all top surface area, divided by the total area of the surface topography, times 100%. This is the same as calculating which percentage of a unit cell comprises the top surface area of the protrusion.

The protrusions cover between 3 and 90% of the surface part, preferably between 5 and 80%, more preferably between 10 and 75% of the surface part, more preferably between 20 and 70%, more preferably between 30 and 65%. Thus, a protrusion covers between 3 and 90% of a unit cell, preferably between 5 and 80% of a unit cell, more preferably between 10 and 75% of a unit cell, more preferably between 20 and 70% of a unit cell, more preferably between 30 and 65% of a unit cell.

The "Valley" Definition

As has been mentioned, the regular pattern of protrusions at the same time defines a pattern of valleys. Thus, the surface topography of the invention may alternatively be defined by a surface part for modulating morphology, proliferation, biochemical functioning, differentiation, attachment, migration, signaling, and/or cell death of a cell population by physical stimulation, comprising a top surface area provided with a regular pattern of valleys defined by a regular pattern of protrusions, which valleys comprise a valley bottom, a first valley wall and a second valley wall, which first valley wall comprises first valley wall sections and optionally first valley wall punctures, and which second valley wall comprises second valley wall sections and optionally second valley wall punctures, wherein said first and second valley wall sections are defined by a side of a protrusion adjacent to the valley, and wherein said first and second valley wall punctures are defined as portions of the valley wall where a line perpendicular to the valley and parallel to the valley bottom does not contact the protrusion adjacent to the valley, and wherein a) the valley wall has a height, defined as the distance normal to the valley bottom from the valley bottom to the top surface area, of 0.5-50 µm;

b) the valley wall profile of the first and second valley wall is independently between 0 and 40 µm.

c) the length of the first and second valley wall sections is independently between 0.01-100 µm.

d) the length of the first and second valley wall punctures, if any, is independently between 0 and 50 µm.

e) the average width of the valley is between 0 and 50 µm.

The top surface area has been defined above, and is the area defined by all top surface areas of the protrusions.

Between the protrusions, a series of valleys is defined. The valleys are defined by two valley walls, which valley walls comprise those sections of the circumferential side face of the protrusions which are adjacent to the valley. The valley wall is the hypothetical straight-line average of those parts of the circumferential side face of the protrusions which are adjacent to the valley, in the direction of the valley. See FIG. 1c and 1d.

Thus, a valley wall comprises valley wall sections, wherein a valley wall section is defined by a side of the protrusion (i.e. one side of a protrusion's circumferential side face) adjacent to the valley. Valley wall sections are thus hypothetical straight lines on the valley wall, of a length defined by the presence of a protrusion. In case of touching protrusions in one direction (i.e. in cases where the average distance between adjacent protrusions in one direction of the regular pattern is 0), the valley wall in that direction comprises only valley wall sections, and no valley wall punctures.

However, in the preferred embodiment where the protrusions are individually spaced protrusions, i.e. with a spacing to all adjacent protrusions such that the average distance in all directions is larger than 0, a valley wall further comprises valley wall punctures.

Valley wall punctures are defined as portions of the valley wall where a line perpendicular to the valley and parallel to the valley bottom does not contact a protrusion adjacent to the valley. As such, it is a portion of the valley wall where there is no valley wall section, i.e. the point in a valley wall where no protrusion is adjacent to the valley. See FIG. 1c and 1d.

Depending on the shape of the protrusions, the first and second valley wall defining a valley may be the same or different, and have the same or different valley wall profile.

The valley bottom is defined as the surface which is located between the protrusions, at the farthest possible distance from the top surface area. The valley bottom may have some slight curvature due to processing, in which case the valley bottom extends from the point where the first valley wall rises to the point where the second valley wall rises. As such, it can also be defined by the average distance between the protrusions which form the valley.

In line with the height of the protrusions, a valley wall has a height, defined as the distance normal to the valley bottom from the valley bottom to the top surface area, of 0.5-50 μm. Preferably, the height of the valley wall is between 1 and 45 μm, more preferably between 2 and 40 μm, more preferably between 3 and 35 μm, more preferably between 4 and 30 μm, even more preferably between 5 and 28 μm, even more preferably between 6 and 28 μm.

A valley wall is defined by the shape of the protrusions adjacent to the valley. As these shapes may be irregular, a valley wall is also defined by the valley wall profile. The valley wall profile, in this respect, is defined as the deviation in the direction normal to the valley wall, and is calculated on the basis of the valley wall sections only. Any valley wall puncture in the valley wall is excluded from the calculation.

The valley wall profile is expressed as the arithmetic mean of the distance of each point of a valley wall section from the valley wall. It is conventionally expressed as $$R_a = \frac{1}{n}\sum_{i=1}^{n}|y_i|$$

wherein $R_a$ is the valley wall profile, and wherein n is the number of data points and wherein $|y_i|$ is a positive number which indicates the distance to the valley wall segment, normal to the valley wall, i.e. normal to the average surface of the valley wall section. The size of n is normally dependent on the resolution of the device used to measure $R_a$, which can for instance be 0.4 μm, in which case n is the length of the valley wall section in μm. $R_a$ can suitably be determined by mathematical analysis of top view images of the surface topography.

The valley wall profile is between 0 and 40 μm, preferably 0.1 and 30 μm, more preferably between 0.5 and 15 μm, even more preferably between 0.8 and 10. A valley wall profile of 0 indicates that all protrusions which define the valley wall have a straight line parallel to the valley, such as may for instance occur in the case of square or rectangular protrusions. Of course, depending on the shape of the protrusions, the valley wall profile of the first and second valley wall may be different. The word "profile", or valley wall profile, as used here, can be equated with the term "roughness", although the term "roughness" is usually applied for the surface roughness of a surface, which is determined by the deviations of the average surface in vertical direction (for a horizontal surface), normal to the surface. In the present case, the valley wall profile is the roughness of the valley wall, i.e. the roughness of a vertical surface comprised on a horizontally oriented topography, which is determined by the deviation of the average valley wall in a direction parallel to the surface topography, and normal to the valley wall.

The length of valley wall sections can be the same as the length of a protrusion in the case when the longest straight-line fitting within the circumference of the top surface area parallel to the surface is parallel to the valley wall. In other cases, a valley wall section is shorter than the length of the protrusion (or protrusion element). As such, the length of valley wall section is 0.01-100 μm, preferably, the length of a valley wall section is 0.05-50 μm, more preferably 0.1-40 μm. Depending on the shape of the protrusions which define the valley, the length of valley wall sections in the two valley walls which define a valley may be the same or different.

The length of the valley wall punctures is generally between 0 and 50 μm, preferably 0.5-40 μm, more preferably 1-30 μm, even more preferably between 2 and 25 μm. Valley wall punctures themselves define a valley, which is oriented perpendicular to the valley of interest. Depending on the shape of the protrusions which define the valley, the length of valley wall punctures in the first and second valley wall may be the same or different.

The average width of the valley is between 0 and 50 μm. The average width of a valley is defined in line with the average distance between protrusions, or protrusion elements, and is calculated by dividing valley wall segments on opposing sides of the valley in line segments of about 0.4 μm, and determining the distance between each line segment of a valley wall section on one side of the valley and the facing line segment of the valley wall section of the adjacent protrusion on the other side of the (same) valley, and then averaging those distances. The average valley width is the average distance between two adjacent protrusions.

The average width of the valley is preferably between 0.5 and 40 μm, more preferably between 1 and 30 μm, more preferably 2 and 25 μm.

Alternatively, the valley width may be defined by the shortest and longest distance between facing protrusions on opposite sides of the same valley, in line with the shortest and longest distance between facing protrusions defined above.

In a much preferred embodiment, the surface topography comprises individually spaced protrusions, which do not touch adjacent protrusions. Thus the distance between protrusions, i.e. the valley width, is larger than 0, and each valley wall comprises valley wall punctures. In this embodiment, a regular pattern of crossing valleys is obtained. In this embodiment, each valley wall comprises valley wall sections and valley wall punctures.

Because it is preferred that the side face of at least a number of the protrusions, or protrusion elements, extends substantially normal to the surface at the position where the side face intersects with the surface, it is also preferred that the valley wall is substantially normal relative to the valley bottom. The angle that a valley wall can have relative to the valley bottom is defined in line with the angle that the circumferential side face may have with the surface.

Thus, in case of a topography comprising only a single type of protrusion comprising a single protrusion element, all valley wall sections have the same profile (which is defined by the circumferential side face of the protrusion adjacent to the valley). In this case, the valley wall sections alternate with valley wall punctures which punctures all have equal length.

In case of topographies comprising protrusions which comprise multiple protrusion elements, or in case of topographies comprising differentially shaped or differentially oriented protrusions, a single protrusion defines multiple valley wall sections which may have a different profile, and multiple valley wall punctures, which may be of non-equal length. In this case, the valley wall sections alternate with valley wall punctures in a regular order.

The Object

The topography as defined above is preferably present on an object having a surface part comprising a metal, polymeric, composite or ceramic material. The surface part may be an exterior or interior surface part of the object. An exterior surface part is a surface part which can be freely contacted by cells which are located at the outside of the object, when the cells are brought into contact with the object. An exterior or interior surface part may include holes, pores or wells.

Suitable materials are known in the art, and include any material which is suitable for the application at hand. That is, for application of a topography of the invention on for instance a reactor, a material suitable to construct a reactor should be used. Similarly, for application of a topography of the invention on an implant, a material suitable to construct an implant should be used. The skilled person knows what type of material is suitable for what type of application, and is capable of choosing an appropriate material accordingly. Examples of suitable materials are titanium (for example for hard (orthopedic or dental) medical implants), polyurethane (for example for abdominal meshes and cosmetic implants), and polystyrene (for example for in vitro culture ware).

An object comprising one (or more) topographies according to the invention can be made by any technique known for creating specifically shaped microstructures onto specific materials. The skilled person knows what types of techniques are suitable for what type of material. Examples of suitable techniques are 3D printing, laser printing, writing, layer-by-layer coating, electrospinning, deposition techniques, spraying and sputtering, stamping, (hot) pressing, (hot) embossing, (nano) imprinting, (injection) molding, casting, etching, laser machining, laser cutting and ablation, (precision) electrochemical machining, (precision) electrochemical gridding and (precision) electrical discharge machining, etc.

The object of the invention is preferably made by laser-machining, precision-technology, engraving, printing, coating, stamping, or etching the topography onto the object. Alternatively, the object may be formed with the topography in a single process, such as by injection molding. Suitable techniques to obtain an object provided with a topography as described are well-known in the art.

Printing may be achieved by employing 3D printing, laser printing and writing surface protrusions on a surface part of a metallic, polymeric, ceramic, composite or other substrate, as is known in the art.

Coating may be achieved by producing the protrusion on a substrate and then coat the surface part using spraying, sputtering, layer by layer coating, electrospinning, or deposition from solutions.

Stamping may be achieved by first producing a mold containing the negative form of the protrusions and then later stamp that mold onto a surface part by using techniques such as pressing, hot press, embossing, hot embossing, imprinting and nanoimprinting. Other techniques including injection molding, processing from a melt, or casting is also possible.

Etching may be achieved by using different solvents in the form of liquid and/or vapor, such as acids and/or organic solvents, as well as a suitable mall, such as to remove portions of the surface part not protected by the mall to obtain the surface topography. Laser machining, engraving and ablation techniques may also be used to carve the topographies into the surface of a suitable material. Precision-technology could include (precision) electrochemical machining, (precision) electrochemical gridding, (precision) electrical discharge machining.

In a much preferred embodiment, the topography comprising a regular pattern of protrusions is a non-separable part of the object. This may be achieved by stamping, printing, etching, coating the topography onto the object or by using other methods mentioned above, for example by forming the object in a single process such as by injection molding.

The surface between the protrusions (valley bottom), the circumferential side face (the valley wall sections) and/or the top surface area of the protrusions may be smooth or substantially smooth, i.e. having a roughness of about 0 (i.e. 0±0.01 µm).

In an optional embodiment however, the surface between the protrusions and/or the top surface area and/or the circumferential side face may have a roughness, commonly abbreviated $R_a$, of 0.01 µm-10 µm, preferably 0.05-8 µm, even more preferably 0.1-5 µm. Also, the roughness may be 0.2-20 or 0.15-3 µm. Roughness, in this respect, is the surface roughness obtained by techniques such as etching, blasting or brushing the surface part prior to or after forming of the topography. The valley wall profile, abbreviated and calculated by the same formula, can thus be seen as the roughness of the valley wall normal to that surface.

The roughness can be determined using atomic force microscopy analysis. A randomly roughened surface part may be obtained by conventional etching, brushing, blasting or the like, of the surface topography comprising a regular pattern of protrusions. Alternatively, a flat surface part, such as a surface part of an implant, may be roughened first, where after the surface topography of the invention is formed.

It is essential that any randomly roughened surface part does still comprise the protrusions of the invention, so that a randomly roughened surface part may not have a roughness which is larger than the height and/or width of the protrusions, so that protrusions with the sizes indicated elsewhere remain present.

The topography of the invention is a surface topography consisting of a multitude of regularly spaced protrusions. Thus, unit cells comprising a protrusion are distributed over the surface part so as to provide a single topography, as defined above. The quantity of unit cells in a single topography is preferably at least 50, more preferably at least 100, even more preferably at least 200, even more preferably at least 500, even more preferably at least 1000. Topographies which extend over a considerable surface part can be of high potential influence on the functioning of large cell collections, such as specific tissue. This is deemed appropriate for in vitro use, such as the growth of cell cultures or tissue, or in vivo use, such as the creation of implants.

A topography of the invention is capable of modulating the cell response, most notably modulating morphology, proliferation, biochemical functioning, differentiation, attachment, migration, signaling, and/or cell death of a cell population by physical stimulation. That is, the topography of the invention is capable of altering the behavior of one or more living cells by inducing changes in morphology, proliferation, biochemical functioning, differentiation, attachment, migration, signaling, and/or cell death. The behavior is altered by physical stimulation.

Physical stimulation in this context means that the signals which induce the change in behavior are transferred by among others shape, hardness and size of the surroundings where the cells are located, i.e. the topography. The "surroundings" of the cell(s) directly modulate the cell(s). Physical stimulation means that the surface topography itself alters the cell response on various aspects, among which cell morphology, proliferation, biochemical functioning, differentiation, attachment, migration, signaling, and/or cell death, and that this response is different for different topographies. By changing a surface topography in contact with a cell or cell population, the cell's morphology, proliferation, biochemical functioning, differentiation, attachment, migration, signaling, and/or cell death can be influenced, all other parameters kept equal.

As an example, a cell culture on a single topography with specific parameters can display minor proliferation, while changing the topography to a different set of parameters may lead to the cell culture displaying high proliferation, under otherwise equal conditions.

The cell(s) of the cell population are located between the protrusions, i.e. within the valleys, of the topography and/or on top of the protrusions, i.e. the top surface area of the topography. This maximizes the physical stimulation of the cell population by the topography.

The physical stimulation which is responsible for the altered behavior is a separate effect from chemical stimulation to alter behavior. In chemical stimulation, the onset of the signals received by the cell to alter behavior is chemically induced through an added compound or through surface chemistry (e.g. choice of bulk material, coating, or surface-functionalization) and is subsequently transferred by signaling molecules which interact with receptors on the cell surface or which enter the cell to interact with receptor molecules within the cell. The mechanism behind the presently observed physical stimulation to alter behavior is still not fully understood, but the examples show that shape of the surface topography, rather than chemical stimulation, are causing the onset of the observed modulation of cell morphology, proliferation, biochemical functioning, differentiation, attachment, migration, signaling, and/or cell death of a cell population. So, the physical stimulation of cells is independent of the chemistry of the surface and/or environment. The altered cell physiological behavior initiated by the physical stimulus of a surface topography might affect the cell's response to and interaction with signaling molecules and receptor molecules.

In the Examples 1-7, the data has been represented showing the effects of various topography-featuring materials, including titanium, polyurethane, and polystyrene, on morphology, proliferation, biochemical functioning, differentiation, attachment, migration, signaling, and/or cell death of a cell population by physical stimulation of different cell types, while the same material without topographies did not similarly modulate the cell behavior.

Modulation of morphology includes changes in cell shape, for example spread or elongated, flat or round, changes in the shape of the nuclei, changes in the cell's or nuclei's size, cell surface area, cell length, cell perimeter, cell aspect ratio and eccentricity, presence of focal adhesion and pseudopodia and organization of the cytoskeleton i.e. actin fibers. In some embodiments, the present surface topographies do not modulate cell morphology, in particular of human mesenchymal stem cells (hMSC's).

The cell cytoskeleton consists of a network of connected fibers and tubules, which form the context of the cytoplasm. Actin microfibers are the main filaments in the cell cytoskeleton. Reorganization of actin fibers within the cell cytoskeleton influences cell shape and cell behavior.

Pseudopodia are extensions of the cell cytoplasm and are formed by cells through reorganization of actin fibers. Pseudopodia are involved in cells functions such as cell movements and uptake of nutrients. Focal adhesions are cellular structures that are used for cell adhesion to the substrate or extra cellular matrix (ECM). Mechanical forces and chemical signals are transmitted from substrate or ECM or other cells to the cells through the focal adhesions. Thus, cell shape appears to influence cell functioning by among others reorientation of pseudopodia and/or focal adhesions.

Morphological changes in the cells are usually observed by bright field- or immunofluorescent microscopy making use of e.g. immunofluorescent (antibody) labeling or histological stainings to visualize the cell cytoplasm, nuclei or specific proteins within cell. Different image analysis software may be used to quantify these morphological observation such as CellProfiler.

Modulation of proliferation includes increased or decreased proliferation or mitosis which may be presented by the following parameters: number of cells, proliferation speed (the ratio of the number of existing cells at a certain time point to the initial number of the cells attached to or seeded onto a substrate or alternatively, the time it takes for one doubling of a cell population), number of cell colonies and the number of cells within such colonies, confluency of the cell layer on the substrate, connection between the cells.

The proliferation parameters may be measured by live or end-stage imaging the cells with or without staining of the cells' nuclei and/or cytoplasm and/or cell membrane components or the like and quantifying the number of the cells using suitable image analysis software such as cell profiler. Other techniques such as lysing the cells and measuring the amount of DNA in the lysate, measuring the metabolic activity of the cells, detaching the cells from substrate and counting them using a manual or automated cell counter may as well be used for quantifying cell proliferation.

In some embodiments, the present surface topographies do not induce modulation of proliferation, in particular of human induced pluripotent stem cells (iPSC's).

Modulation of biochemical functioning includes all chemical processes and reactions that happen within or related to the cells. These processes include biosynthesis and cell metabolism, protein synthesis, protein transcription and protein secretion, enzymatic reactions and enzyme expression, biochemical transportation through membrane channels and receptors, cell signaling, and a cell's immune response.

Modulation of differentiation includes differentiation towards a certain cell type, maintaining a differentiated or undifferentiated phenotype, maintaining a specific function, dedifferentiation from a differentiated cell type, as well as redifferentiation towards another cell type.

Stem cells or progenitor cells changing to a more differentiated cell type is called differentiation. Differentiated cells express specific protein markers and functions. Differentiated cells may maintain the same phenotype, lose their differentiated phenotype and turn into undifferentiated cells (dedifferentiation) or change into another differentiated cell type (redifferentiation).

Various known molecular biology techniques are used to analyze cell biochemical functioning and differentiation state. For example, differentiation of cells can be characterized by imaging the cells using immunofluorescent labeling (antibody labeling) of (combinations of) differentiation-specific proteins combined with fluorescence microscopy or fluorescence-activated cell sorting (FACS). Other techniques may be used to quantify the expression of specific markers of certain cell types at protein or gene level including quantitative polymerase chain reaction (qPCR), or enzyme-linked immunosorbent assay (ELISA).

Modulation of cell attachment includes increased or decreased number of the cells attached to a substrate, formation of tight junction between the cells, formation of focal adhesion, secretion of proteins involved in cell attachment, detachment of the cells from the surface, detachment of cells from each other, attachment strength of a cell to the surface, an the like.

Modulation of cell attachment can be measured by immunofluorescent labeling of the cell cytoplasm or focal adhesion proteins, (bright field, fluorescence or scanning electron) microscopy techniques and imaging of the cells, lysing the cells and measuring the amount of DNA in the lysate, measuring the metabolic activity of the cells, detaching the cells from substrate and counting them using a manual or automated cell counter, etc. Modulation of cell attachment is important in any application were adherent cells are involved. Cell attachment is one of the primary steps of cell interactions with biomaterials and basically affects all future interactions between cells and biomaterials. For examples, biomaterials that promote the attachment of macrophages may affect the level of encapsulation with fibrous tissue. Biomaterials with lower attachment of blood platelets may suppress blood coagulation.

Modulation of cell migration includes (micro) movements of cells in a certain area or their movements towards or relocation to different areas.

Modulation of cell migration can be measured by live imaging, time-lapse microscopy, fluorescent labeling, etc. Modulation of cell migration can affect all states of tissue development such as embryonic and adult tissue formation, tissue regeneration and turnover, developing therapeutic strategies, wound and defect healing and immune response.

Modulation of cell signaling includes regulating any physical or chemical interaction between cells (cell-cell interaction), gene expression, protein production and secretion.

Modulation of cell signaling can be measured by quantifying biomarkers expressed or secreted from living cells using techniques such as immunofluorescent staining, qPCR, ELISA, Western blot, etc.

Modulation of cell signaling can affect all processes that govern cell fate and response to foreign biomaterials including morphology, proliferation, biochemical functioning, differentiation, attachment, migration and cell death.

Modulation of cell death includes increasing or decreasing cell apoptosis (programmed cell death), necrosis, mitotic catastrophe or death of cellular components (autophagy).

Modulation of cell death such as apoptosis can be measured by live-dead assay, counting the number of cells, immunofluorescent staining of apoptosis markers, etc.

Modulation of cell death such as apoptosis or necrosis can affect systems developed for supporting the culture and growth of living cells or in developing cure methods for diseases and cancer therapy.

In preferred embodiments, modulation of cell morphology, proliferation, biochemical functioning, differentiation, attachment, migration, signaling, and/or cell death of a cell population by physical stimulation includes modulation of cell morphology, proliferation, biochemical functioning, differentiation and attachment. In preferred embodiments, modulation of the cell response includes modulation of cell morphology. In other preferred embodiments, modulation of the cell response includes modulation of cell proliferation. In other preferred embodiments, modulation of the cell response includes modulation of cell biochemical functioning. In other preferred embodiments, modulation of the cell response includes modulation of cell differentiation. In other preferred embodiments, modulation of the cell response includes modulation of cell attachment.

In some embodiments, modulation of cell morphology, proliferation, biochemical functioning, differentiation, attachment, migration, signaling, and/or cell death of a cell population by physical stimulation of a cell population does not include physically stimulating human mesenchymal stem cells (hMSC) to modulate differentiation, most notably inhibiting adipogenic differentiation. In other embodiments, such modulation does not include physically stimulating kidney epithelial cells by modulation of cell attachment, proliferation and morphology, or by modulation of cell morphology, adherence and function. In still other embodiments, such stimulation does not include physical stimulation of induced pluripotent stem cells (iPSC) to maintain pluripotency proliferation in vitro.

A cell population that can be used with topographies of the invention is not particularly limited. The cell population comprises one or more living cells, in a suitable culture medium when required. The cell population may comprise a single cell type, but also multiple cell types, such as in a cell co-culture or in living tissue.

The cell population is a population of eukaryotic cells, such as originating from humans, plants, animals, protists, yeasts and fungi. Cells may be derived from any plant, microorganism, or animal, and may be from any type.

In some embodiments, the cells are not human iPSC's. In other embodiments, the cells are not hMSC's.

Mammalian cells are preferred, in particular cells from human, monkey, bovine, pig, rat or mouse. Further preferably, mammalian cells include mesenchymal stem cells, adipose-derived stem cells, osteoblasts, immune-response related cells, among which preferably macrophages, and hepatocytes, Cells may be obtained in any known way, such as by isolation from tissue of a living or deceased donor, by cell culturing, by differentiation of cell types with higher potency, by dedifferentiation from cell types with a more progressed differentiation state or by redifferentiation from cell types with a different differentiation state. Cell isolation from tissues or biopsies include digestion of the extra cellular matrix of the cells by one or more enzymes for example collagenase. Since most of the time, tissues consist of different cell types or cell populations, generally the next step in cell isolation includes purification of the cells. Other techniques may be used to obtain cells depending on the cell type. For example, blood cells may be obtained by centrifuging the whole blood and collecting the separated layers containing different types of cells.

An object of the invention can be used in conjunction with suitable culture medium, as is known in the art. Such culture medium comprises water, and may additionally comprise proteins such as fetal bovine serum (FBS) and growth factors, amino acids, vitamins, glucose, inorganic salts and antibiotics and the like. For in vitro application of an object of the invention, use of suitable culture medium is preferred. In other conditions, the cells may be cultured in other liquids such as phosphate buffered saline (PBS), water, or on a gel such as Matrigel or agarose gel, on a coating such as collagen, laminin, fibronectin, fibrinogen, or polyamine or be embedded into a biomaterial such as a hydrogel or polymer carrier. Cells may be fixed using fixation solution and analyzed in a wet or dry condition.

The invention furthermore pertains to a method to modulate morphology, proliferation, biochemical functioning, differentiation, attachment, migration, signaling, and/or cell death of a cell population by physical stimulation, comprising 1) contacting one or more cells in a suitable medium with a surface part provided with a regular pattern of protrusions, the regular pattern of protrusions defined by a grid of intersecting gridlines which can be laid over the surface part, which gridlines define a pattern of unit cells, such that each unit cell comprises a maximum of one protrusion, which protrusions comprise one or more protrusion elements, which protrusion elements are defined as surface portions elevated above the surface having a top surface area and a circumferential side face connecting the top surface area with the surface, wherein each protrusion element has a maximum height of between 0.5 and 50 µm above the surface, and wherein
   a) the average distance between adjacent protrusions is between 0 and 50 µm;
   b) the top surface area of the protrusion is between 1 and 6000 µm$^2$; and
   c) the protrusions cover between 3 and 90% of the surface;
2) allowing the cells to respond to the surface.

The method can be adapted for each specific application purpose described below. The method can be an in vivo method, but is preferably an in vitro method.

Objects of the invention can be used in vivo or in vitro.

In one embodiment, an object of the invention modulates morphology, proliferation, biochemical functioning, differentiation, attachment, migration, signaling, and/or cell death of a cell population by physical stimulation in vitro. In vitro use comprises for instances the culturing of cells on a surface part comprising the topography as defined above. In this embodiment, cells cultured on or in the object of the invention are, direct or indirect, physically stimulated to alter their behavior.

For example, the object may be for instance an object for the culturing of cells such as a culture flask, plate, dish, slide, bottle, chamber or bag, comprising a surface for cell culturing, which surface comprises a topography as defined above.

Topographies on objects for in vitro use may be of various sizes. For example, culture flasks may have a topography-featuring surface with a surface area of 5-10000 cm$^2$, preferably 10-5000 cm$^2$, more preferably 15-1000 cm$^2$, and topography-featuring surface present inside the wells of a culture plate usually have a surface area of 0.01-10 cm$^2$ per well.

The invention furthermore pertains to use of an object of the invention, for in vitro modulating morphology, proliferation, biochemical functioning, differentiation, attachment, migration, signaling, and/or cell death of a cell population by physical stimulation. The object can be adapted for use for each specific application purpose described below.

In another embodiment, an object of the invention is adapted for in vivo use. Such an embodiment is preferably an implant which is preferably provided with a topography to modulate cell biochemical functioning, cell attachment or differentiation by physical stimulation, as described above.

In one embodiment of in vivo use, the invention pertains to a method for treating a patient by application of an object as defined above, by either definition, for modulating morphology, proliferation, biochemical functioning, differentiation, attachment, migration, signaling, and/or cell death of a cell population by physical stimulation. Such methods may be based on objects provided with topographies for each specific application purpose described below.

In another embodiment of in vivo use, the invention pertains to an object as defined above, by either definition, for use in modulating morphology, proliferation, biochemical functioning, differentiation, attachment, migration, signaling, and/or cell death of a cell population by physical stimulation. The object may be for use in any of the specific application purposes described below.

In yet a further embodiment of in vivo use, the invention pertains to use of an object as defined above, by either definition, in modulating morphology, proliferation, biochemical functioning, differentiation, attachment, migration, signaling, and/or cell death of a cell population by physical stimulation. The object may be used for any of the specific application purposes described below.

In still another preferred embodiment of in vivo use, the invention pertains to use of an object as defined above, by either definition, in the manufacture of a medicament for modulating morphology, proliferation, biochemical functioning, differentiation, attachment, migration, signaling, and/or cell death of a cell population by physical stimulation. The medicament may be targeted for any of the specific application purposes described below.

All of the above generically defined aspects and parameters of the invention may be combined with other aspects and parameters defined above. In addition, each and every generically defined aspect and parameter defined above is also applicable for each specific application purpose defined below, unless that aspect or parameter is described specifically for an application purpose using different wording or parameters than used above. In such a case, aspects and parameters defined for a specific application purpose below overrule the generic definition of the same aspect or parameter defined above.

Embodiments for Specific Application of a Cell Response

In one embodiment, an object of the invention comprises on its surface part preferably one, but no more than 10, different topographies. That is, in this embodiment, an object of the invention comprises at most 10, preferably at most 9, more preferably at most 8, more preferably at most 7, more preferably at most 6, more preferably at most 5, more preferably at most 4, more preferably at most 3, more preferably at most 2, and most preferably 1 topography. In this embodiment, a topography may have a length, width or diameter of 1 µm to 10 m. The surface area of such a topography may be from 1 µm$^2$ to 100 m$^2$, depending on the application.

In this embodiment, one (or at most a few) selected topographies are used, to promote a cell response by physical stimulation, for a particular application. A topography may have any shape. Applications may include but are not limited to objects for the culturing of cells including culture wares or culture platforms (e.g. chips or microfluidic devices), bioreactors, membranes or implants. The skilled person can come up with countless ways to apply the topographies of the invention.

Advantages of the invention include but are not limited to accurate modulation of the cell response, physical stimulation without the need to use growth factors or (protein) coatings, flexibility of the approach to be applied to different materials and products, no leaching or layer defects, and no batch to batch difference.

In another embodiment for specific application of a cell response, an object of the invention is adapted for in vivo use. Such use may comprise an object provided with a topography, which is implanted or temporarily inserted into a living body. In this case, the object is preferably an implant. Thus the invention furthermore pertains to an object as defined above for use as an implant.

An implant may be a temporary implant or a durable implant. A temporary implant is an implant which remains in the body for a limited duration, and which may be taken out of the body after having exerted its purpose, or which may degrade slowly in the body, as is known in the art. A durable implant is an implant which in principle should remain in place indefinitely, although this may be subject to lifetime-factors (e.g. wear) of the implant in question.

The invention furthermore pertains to methods to treat a subject in need of an implant with an implant comprising a topography as defined above. An implant of the invention can be for example an orthopedic or a dental implant, a liver implant or an implant controlling the immune response. Other implants according to the invention can be muscular implants, nervous system implants, electro-stimulating implants including spinal cord stimulator implants, electro-acoustic implants, deep brain stimulators, pacemaker implants, cosmetic implants, breast reconstruction implants, (abdominal) mesh implants. Such implants require proper regulation of the immune response.

For embodiments of the invention which are implants, it is a distinct advantage that implants provided with a surface topography of the invention modulate cells to provide a desired response. This allows for instance for modulated ingrowth of the surrounding tissue, modulated differentiation of surrounding cells, or modulated cell attachment. In the case of orthopedic or dental implants, an advantage can be increasing the formation/ingrowth of new bone leading to better fixation of the implant in or onto bone or tooth tissue.

Alternatively, this allows for instance for a decreased immune response against an implant, with the advantage of decreasing problematic encapsulation of an implant with fibrous tissue or rejection of the implant. Further alternatively, this allows for instance for increasing attachment and proliferation of endothelial cells, with the advantage of having a functional monolayer of endothelial cells on the surface of the implant to, among others, avoid blood clotting and thrombosis. Further alternatively, this allows for increased proliferation and maintaining the phenotype of hepatocyte cells, with the advantage of increasing the long time viability and functionality of the cells.

Implants according to the invention can be made by any of the techniques described above, as is known in the art. Examples of suitable techniques to provide objects with a topography are described above.

For each specific application purpose defined below, topographies comprising protrusions with a specific shape will be described as "hit" topographies. These topographies are shown in tables in the Example section. Each aspect and parameter recited under the generic description above and/or under a specific application purpose described below may apply to each hit topography, unless otherwise mentioned.

The hit topographies reflect the protrusion shape which has an optimal effect in that application purpose. However, it is reasonable to assume that the effect of a topography, for each application purpose, is the same for topographies with are of similar shape as a hit topography. Whether a shape is similar or not is essentially judged by comparison by eye. It may be numerically expressed by defining the center point of a protrusion mathematically, as is known in the art. The distance from that center point to any specific point on the circumferential side face is then called the radius toward that specific point. A shape is similar if, when overlaying the similar shape by aligning the central points of the compared shapes and orienting the shapes so as to match as closely as possible the shape of the hit topography, the radius of the similar shape deviates from the radius of the hit topography on any point of its circumferential side face by not more than 10%, preferably not more than 5%, more preferably not more than 2.5%, even more preferably not more than 1%.

Hepatocytes

In one embodiment, an object of the invention can be an object for modulating hepatocytes. Hepatocytes, in this context, are defined as the main cells found in liver tissue and they are involved in most of the biochemical functions of the liver and may originate from any human or animal, including rhesus monkey, mice, etc. as described above. Hepatocytes in this context also refers to hepatocyte progenitor cells, and hepatocyte-like cells (such as immortalized cell lines like Hep G2).

In this embodiment, the topography is defined by
a) the average distance between adjacent protrusions is between 0-50 µm, preferably 0.5-40 µm, more preferably 1-30 µm, even more preferably 3-25 µm;
b) the top surface area of the protrusions is between 1-6000 µm$^2$, preferably 10-3000 µm$^2$, preferably 15-1500 µm$^2$, more preferably 17-1000 µm$^2$, even more preferably 20-250 µm$^2$; and
c) the protrusions cover 3-90%, preferably 5-50%, more preferably 7-40%, even more preferably 8-35% of the surface part.

In addition, a topography can be defined by a length of the protrusions/protrusion elements of 0.01-100 µm, preferably 0.5-50 µm, more preferably 1-40 µm, even more preferably 2-35 µm, and a width of the protrusions/protrusion elements of 0.01-100 µm, preferably 0.5-50 µm, more preferably 1-35 µm, even more preferably 4-23 µm.

Alternatively, an object for modulation of hepatocytes according to the invention can be defined by
a) a valley wall height, defined as the distance normal to the valley bottom from the valley bottom to the top surface area, of 0.5-50 µm, preferably 1-40 µm, more preferably 2-35 µm, more preferably 4-30 µm, even more preferably 5-28 µm;
b) the valley wall profile of the first and second valley wall is independently 0-40 µm, preferably 0.1-35 µm, more preferably 0.5-30 µm, even more preferably 1-20 µm.
c) the length of the first and second valley wall sections is independently 0.01-100 µm, preferably 0.1-50 µm, more preferably 1-40 µm, even more preferably 2-32 µm.
d) the length of the first and second valley wall punctures, if any, is independently between 0-50, preferably 0.2-40, more preferably 0.5-35 µm.
e) the average width of the valley is between 0-50 µm, preferably 0.5-40 µm, more preferably 1-30 µm, even more preferably 3-25 µm;

Thus, the invention also pertains to a method to modulate morphology, proliferation, biochemical functioning, differentiation, attachment, migration, signaling, and/or cell death of a cell population by physical stimulation as defined above, wherein the living cells are hepatocytes, and wherein the topography is as defined above.

Any material may be used to make the object, but preferably, the object, or at least the surface part thereof which is provided with the topography, is made of a glass, metal or polymeric material, even more preferably, polymeric material. Most preferably, the object comprises a surface part comprising polystyrene, polypropylene, collagen, laminin, polyamine, and hydrogels like Matrigel, and agarose gel.

Suitable culture media for this embodiment includes, but is not limited to, one or more of the components: water, glucose, proteins, amino acids, vitamins, penicillin, antibiotics, and inorganic salts.

Modulation of hepatocytes includes stimulating hepatocyte-like morphology, proliferation of hepatocytes in shorter time and/or for more cycles, maintaining hepatocytes in culture for a longer period of time while retaining phenotype and hepatocyte-characteristic functionality, stimulating hepatocyte attachment in early and late time points, and preventing early cell death. This functionality can be ascertained by evaluation of functional biomarkers of hepatocytes including detoxification markers including cytochrome protein (CYPs), Albumin, E-cadherin, CD81, etc. The expression of these markers can be evaluated at gene and protein level using various techniques such as qPCR, ELISA, immunofluorescent staining, western blot and fluorescent-activated cell sorting (FACS).

A group of surface topographies has been identified that were able to support in vitro culture of functional hepatocytes for an extended period of time while retaining their phenotype. The topographies were embedded into polystyrene (PS) substrates, and were used with and without addition of a collagen coating, and were examined for their interaction with hepatocytes using conventional cell culture techniques.

The selected topography-featuring samples allowed for higher cell attachment compared to sample without such surface topography. Hepatocytes from both rhesus macaque as well as human origin could be maintained in in vitro culture for at least 1 month, when cultured on the topography-embedded substrates, both of PS with and without collagen coating on the surface. This while the current gold standard, i.e. collagen sandwich culture (double layer of collagen where the hepatocytes are cultured in between), can support in vitro culture of hepatocytes for maximum of 8-10 days. Hepatocytes cultured on the topography-embedded substrates were characterized for functionality and found to be fully functional, i.e. proper expression of hepatocyte-specific markers, including over 10 detoxification and metabolic activity markers. Hepatocytes cultured on topography-embedded substrates without collagen coating express similar or even higher levels of the analyzed hepatocyte-specific markers compared to the topography-embedded substrates with collagen coating, proving the selected topographies make the expensive, laborious and easy-to-fail coating with collagen redundant. Similarly, it was shown that hepatocytes seeded onto the topographies-embedded substrates, again with and without collagen coating, could be successfully infected with malaria parasites and be maintained in culture for 1 month, showing the effectiveness of the surface topographies in supporting in vitro culture of hepatocytes under pathologic conditions.

In another embodiment, hepatocytes are modulated in vivo. In this embodiment, an object of the invention can be a liver implant. In this embodiment, the parameters average distance, top surface area, coverage, length and width in the "protrusion" definition and the parameters valley wall height, valley wall profile, length of valley wall sections and punctures, and average width of the valley, are as defined above for in vitro culturing of hepatocytes.

A liver implant according to the invention can be an object which has at least one surface part, provided with a surface topography as defined, and may be provided with hepatocytes. Preferably, the implant is furthermore provided with means to retain hepatocytes on the surface part provided with the topography.

Suitable means to retain hepatocytes on the surface part provided with the topography include for example a hydrogel layer, a polymeric layer, a protein coating, or the like. Preferably, such layers allow for diffusion of nutrients and other essential components for cell functioning in vivo to reach the hepatocytes on the object, and/or provide better cell attachment to the surface.

A liver implant may comprise multiple surface topographies, for example up to 10, on the surface part in order to modulate the biological response of hepatocytes and other type of cells involved in the liver's functions.

A liver implant may also be a 3D scaffold, preferably made of materials as defined above, and is porous, comprising one or more surface topographies on the surface parts, providing a suitable environment for hepatocyte growth and tissue formation.

An advantage of a liver implant provided with a topography as defined above is that it will restore or enhance the functions of the liver including metabolizing and detoxifying biochemical compounds produced by the body or introduced to the body such as drugs.

Further use of the topographies of the invention for modulating hepatocytes includes for example artificial livers, 3D scaffolds for liver regeneration, drug screening platforms, and biosensors. These devices can be produced using different techniques as mentioned above and may comprise 1-10 modulating surface topographies on the surface parts. For in vivo use, the objects can be introduced into a body with or without cells, such as cells from a donor, autologous cells cultured in a lab environment or cells of a different source.

Osteogenesis

In this embodiment, an object of the invention is an orthopedic or dental implant, in which modulating the cell response, most notably morphology, proliferation, biochemical functioning, differentiation, attachment, migration, signaling, and/or cell death of a cell population by physical stimulation is the modulation of osteogenic biochemical functioning, differentiation, and attachment. Cells of which the cell response is modulated in this embodiment are preferably osteoblasts.

This embodiment pertains to an object such as a medical device for stimulating osteogenesis, preferably an implant, for implanting in or on human or animal bone or tooth, which is an artificially made substitute for natural tissue, mimicking natural tissue. The implant, which is a biomedical implant, is preferably implanted in or on human or animal bone or tooth. In one preferred embodiment, the implant is implanted into human bone or tooth. In another preferred embodiment, the implant is implanted into animal bone or tooth.

Bone is a natural mineralized structure synthesized by osteoblasts, which has the function of providing strength and support to the body of vertebrates. Also, bone provides a solid support for the attachment of muscle, so as to allow movement of the body.

Bone generally is said to exist in two types: cortical bone tissue is the hard outer layer of a bone, and has a smooth, white, glistening appearance. It consists of a dense network of microscopic columns, in which osteoblasts and mineralized tissue are present.

Cancellous bone, also known as spongy bone, is found on the inside of a bone, and consists of a more or less porous network of bone tissue. In the spaces between the bone tissue, bone marrow and stem cells are present as well as blood vessels to provide nutrients to the living cells inside the bone.

Tooth are small structures made of highly calcified tissues found in the jaws of human and other vertebrates, playing important roles in chewing and in speech. Teeth have two parts, one inside and one outside the gums respectively called root and crown. There are different layers in tooth tissue including: Enamel which is the hardest and the outer layer of the tooth mostly made of calcium phosphate, dentin which is the layer underlying the enamel which is made of living cells in a hard mineral matrix, pulp which is a softer inner structure of teeth containing living cells, blood vessels and nerves, cementum, the layer that firmly connects the roots of the teeth to the gums and jaw, and finally periodontal ligament that is also involved in holding the teeth in the jaw bone.

Bone and tooth tissue, like most other tissue types, is continuously formed and degraded. Due to the mineralized environment, the rate of formation and degradation of bone and tooth tissue is relatively slow in comparison to most other tissue types. Therefore, when a defect occurs, regeneration of bone or tooth tissue takes a longer time than regeneration of other tissue types. In addition, when large bone or tooth segments are defect or absent, regeneration may not be possible.

In such cases, an implant according to the invention may be implanted in or onto the bone or tooth. This affects restoration of the natural function of the body part. Preferably, for a bone implant, the implant is at least partially implanted into cortical bone. The tooth implant is preferably implanted into the jaw bone or tooth tissue. The implant of the invention, by its specific topography defined below, stimulates osteogenesis and therewith fixation of the implant to the bone or tooth by tissue ingrowth.

Tissue ingrowth in the present context is understood to mean the process of bone or tooth formation onto and/or into the implant, preferably at the boundary where natural bone or tooth tissue and the implant connect. When implanting the implant in or onto natural bone or tooth, there is a small gap at this boundary, which in time may be filled by natural bone or tooth tissue which is formed by cells which naturally form such tissue, such as the osteoblasts, ameloblasts, odontoblasts or cementoblasts present in the natural bone or tooth tissue in the gap at the boundary with the implant. As such, tissue ingrowth is growth of natural bone or tooth tissue onto or into the implant, which fixates the implant onto or into the bone or tooth tissue on or in which the implant is implanted.

The topography of the invention stimulates osteogenesis, preferably therewith increasing the fixation of the implant in or onto bone or tooth tissue. Increased fixation means that the process of bone formation in the gap is accelerated, and/or that the strength with which the implant is fixed in or onto the bone or tooth is increased. Also, increased fixation may mean that the fixation between surrounding bone or tooth tissue and the implant provided by ingrown natural tissue holds longer, so as to avoid or postpone implant replacement.

Increased bone formation can be measured by various means, such as by analyzing the quantity of alkaline phosphatase enzyme (ALP), Osteocalcin (OC), Osteopontin (OP) and/or Bone sialoprotein (BSP) present in for instance stem cells which are grown in on the topography in vitro.

Fixation strength can be measured by performing in vivo tests followed by determining the force required to pull the implant from the implantation site.

The topography of the invention is present on an object such as a medical device for stimulating osteogenesis, preferably an implant, which is to be implanted in or onto bone or tooth, at locations where tissue ingrowth is wanted. Preferably, all locations of the implant which would benefit from increased fixation to natural bone or tooth tissue are covered with the topography of the invention.

In a preferred embodiment, the device of the invention is to be implanted in or onto human or animal bone, preferably human bone. In this case, the implant is called an orthopedic implant.

In an alternative preferred embodiment, the device of the invention is to be implanted in or onto human or animal jaw bone or tooth, preferably human jaw bone or tooth. In this case, the implant is called a dental implant.

In this embodiment, a topography present on the object of the invention can be defined by a) the average distance between adjacent protrusions is between 0-50 µm, preferably 0.5-40 µm, even more preferably 1-30 µm, even more preferably 2-25 µm.

b) the top surface area of the protrusion is between 1 and 6000 µm$^2$, preferably 10 and 3000 µm$^2$, more preferably between 20 and 1500 µm$^2$, more preferably between 25 and 1000 µm$^2$, even more preferably between 30 and 750 µm$^2$; and c) the protrusions cover between 3 and 80% of the surface part, preferably between 10 and 75% of the surface part, more preferably between 20 and 70%, more preferably between 30 and 65%.

In addition, the length of a protrusion in a topography wherein the protrusions comprise only one protrusion element can be 0.01-100 µm, preferably, 0.5-50 µm, more preferably 1-40 µm, and the length of a protrusion in a topography wherein the protrusions comprise multiple protrusion elements can be 0.01-100 µm, preferably 0.1-45 µm, more preferably 0.5-40 µm, even more preferably 1-30 µm.

The width of a protrusion in a topography wherein the protrusions comprise only one protrusion element can be 0.01-100 µm, preferably 0.5-50 µm, more preferably 1-40 µm, and the width of a protrusion in a topography wherein the protrusions comprise multiple protrusion elements can be 0.01-100 µm, preferably 0.1-45 µm, more preferably 0.5-40 µm, even more preferably 1-30 µm.

Alternatively, an orthopedic or dental implant can be defined as an object having at least one topography wherein
 a) the valley wall height is 0.5-50 µm, preferably between 1 and 40 µm, more preferably between 2 and 35 µm, more preferably between 4 and 30 µm, and even more preferably between 5 and 28 µm.
 b) the valley wall profile is between 0 and 40 µm, preferably 0.1 and 30 µm, more preferably between 0.5 and 15 µm, even more preferably between 0.8 and 10 µm.
 c) the length of valley wall sections is 0.01-100 µm, preferably 0.05-50 µm, more preferably 0.1-40 µm.
 d) the length of valley wall punctures is between 0 and 50 µm, preferably between 0.5 and 40 µm, more preferably between 1 and 30 µm, even more preferably between 2 and 25 µm.
 e) the average width of the valley is between 0 and 50 µm, preferably between 0.5 and 40 µm, more preferably between 1 and 30 µm, more preferably 2 and 25 µm.

An advantage of an orthopedic or dental implant according to the invention is that it improves fixation of the implant to the surrounding natural (bone and tooth) tissue.

An orthopedic implant is a medical device manufactured to replace a missing joint or bone or to support damaged bone. Examples of suitable orthopedic implants which may benefit from including a surface topography as presently described, include a knee replacement implant, femoral component and tibial stemmed plate, (total) hip replacement implant femoral stem and acetabular shell, elbow and finger implant stems and hinges, maxillofacial implants, skull implant, shoulder implants, ankle implants, (external) fixation implants such as nails, screws, pins, rods and plates, implants used in infusion spinal revision including spinal cages, spinal discs, pedicle screws and rods and cervical vertebra plates.

Preferably, the orthopedic implant is a knee replacement implant femoral component and tibial stemmed plate, (total) hip replacement implant femoral stem and acetabular sell, and implants used in infusion spinal revision including spinal cages, spinal discs, pedicle screws and rods and cervical vertebra plates.

A dental implant is a surgical component that interfaces with the bone of the jaw or skull to support a dental prosthesis such as a crown, bridge, denture, facial prosthesis or to act as an orthodontic anchor. Examples of suitable dental implants which may benefit from including a topography as presently described, include jaw and maxillofacial implants, dental plates and frameworks, dental base screws and post screws, crown implants. Preferably, the dental implant is a dental plate and framework, a dental base screw or a post screw.

The objects for modulation of osteogenic biochemical functioning, differentiation, and attachment described above can be made by any known method for the fabrication of implants. Such methods are generally described above, and known in the art.

Immunoregulation

In another embodiment, modulation of the morphology, proliferation, biochemical functioning, differentiation, attachment, migration, signaling, and/or cell death of a cell population by physical stimulation comprises immunoregulation. Immunoregulation in this context means regulating the immune response to foreign objects implanted into or present in the body, i.e. the foreign body response. Immunoregulation includes controlling foreign body giant cell (FBGC) formation, the inflammation response, macrophage involvement, fibrosis and encapsulation of the foreign body. As such, the invention furthermore provides objects for immunoregulation of immune cells, wherein the topography is as defined above.

The immune response has an (early stage) immediate response followed by a more constant, stable, end stage. The early stage, acute response is highly important in controlling the acceptance of a foreign object (biocompatibility) and is also an important driver for the (chronic) immune activity level in the end stage. It is believed that the initial response needs to be of an appropriate, but controlled, level to allow for proper but minimal encapsulation and an inactive (non-inflammatory) end stage. The exact mechanisms are, however, not yet fully understood. In preferred embodiments, three classes of immunoregulating topographies can be defined: (1) a low immune response in the early stage combined with a low response in the later stage, from here on referred to as L/L; this can also be referred to as decreasing the immune response. (2) a high immune response in the early stage combined with a high response in the later stage, from here on referred to as H/H and; this can also be referred to as increasing the immune response (3) a high immune response in the early stage combined with a low response in the later stage, from here on referred to as H/L.

In preferred embodiments, a topography of the L/L type for modulating the immune response can be defined by
 a) the average distance between adjacent protrusions is between 0-50 µm, preferably 0.5-40 µm, more preferably 1-20 µm, even more preferably 2-12 µm; and
 b) the top surface area of the protrusion is between 1 and 6000 $µm^2$, preferably 10 and 3000 $µm^2$, more preferably between 15 and 1500 $µm^2$, more preferably between 20 and 1000 $µm^2$, even more preferably between 20 and 200 $µm^2$, most preferably 25-200 $µm^2$; and
 c) the protrusions cover between 3 and 90% of the surface part, preferably between 5 and 80%, more preferably between 10 and 75%, even more preferably between 26 and 50%.

In addition, the length of a protrusion in a topography wherein the protrusions comprise only one protrusion element can be 0.01-100 µm, preferably 0.5-50 µm, more preferably 1-50 µm, even more preferably 2-40 µm, and the length of a protrusion in a topography wherein the protrusions comprise multiple protrusion elements can be 0.01-100 µm, preferably 0.1-45 µm, more preferably 0.5-40 µm, even more preferably 1-30 µm.

The width of a protrusion in a topography wherein the protrusions comprise only one protrusion element can be 0.01-100 µm, preferably 0.5-50 µm, more preferably 1-50 µm, even more preferably 2-40 µm, and the width of a protrusion in a topography wherein the protrusions comprise multiple protrusion elements can be 0.01-100 µm, preferably 0.1-45 µm, more preferably 0.5-40 µm, even more preferably 1-30 µm.

Alternatively, an immunoregulating implant of the L/L type can be defined as an object having at least one topography wherein
 a) the valley wall height is 0.5-50 μm, preferably between 1 and 40 μm, more preferably between 2 and 35 μm, more preferably between 4 and 30 μm, and even more preferably between 5 and 28 μm.
 b) the valley wall profile is between 0 and 40 μm, preferably 0.1 and 35 μm, more preferably between 0.5 and 30 μm, even more preferably between 1 and 20 μm.
 c) the length of valley wall sections is 0.01-100 μm, preferably 0.1-50 μm, more preferably 1-40 μm, even more preferably 2-32 μm.
 d) the length of valley wall punctures is between 0 and 50 μm, preferably between 0.2 and 40 μm, more preferably between 0.5 and 35 μm.
 e) the average width of the valley is between 0-50 μm, preferably 0.5-40 μm, more preferably 1-20 μm, even more preferably 2-12 μm.

Such topographies are capable of lowering the immune response to a foreign object, preferably minimizing the encapsulation tissue and inflammatory activity around a foreign object.

In addition, objects of the invention can be used to stimulate the immune response to a foreign object, preferably strengthening the controlled encapsulation of a foreign object.

Topographies which can be used in this embodiments are topographies of the type H/H, which can be defined by
 a) the average distance between adjacent protrusions is between 0-50 μm, preferably 0.5-40 μm, more preferably 2-20 μm, even more preferably 5-12 μm; and
 b) the top surface area of the protrusion is between 1 and 6000 μm$^2$, preferably 10 and 3000 μm$^2$, more preferably between 20 and 1000 μm$^2$, more preferably between 25 and 250 μm$^2$, even more preferably between 20 and 70 μm$^2$; and
 c) the protrusions cover between 3 and 90% of the surface part, preferably between 5 and 50%, more preferably between 10 and 40%, even more preferably between 15 and 25%

In addition, the length of a protrusion in a topography wherein the protrusions comprise only one protrusion element can be 0.01-100 μm, preferably, 0.5-50 μm, more preferably 1-50 μm, even more preferably 2-40 μm, and the length of a protrusion in a topography wherein the protrusions comprise multiple protrusion elements can be 0.01-100 μm, preferably 0.1-45 μm, more preferably 0.5-40 μm, even more preferably 1-30 μm.

The width of a protrusion in a topography wherein the protrusions comprise only one protrusion element can be 0.01-100 μm, preferably 0.5-50 μm, more preferably 1-50 μm, even more preferably 2-40 μm, and the width of a protrusion in a topography wherein the protrusions comprise multiple protrusion elements can be 0.01-100 μm, preferably 0.1-45 μm, more preferably 0.5-40 μm, even more preferably 1-30 μm.

Alternatively, an immunoregulating implant of the H/H type can be defined as an object having at least one topography wherein
 a) the valley wall height is 0.5-50 μm, preferably between 1 and 40 μm, more preferably between 2 and 35 μm, more preferably between 4 and 30 μm, and even more preferably between 5 and 28 μm.
 b) the valley wall profile is between 0 and 40 μm, preferably 0.1 and 35 μm, more preferably between 0.5 and 30 μm, even more preferably between 1 and 20 μm.
 c) the length of valley wall sections is 0.01-100 μm, preferably 0.1-50 μm, more preferably 1-40 μm, even more preferably 2-32 μm.
 d) the length of valley wall punctures is between 0 and 50 μm, preferably between 0.5 and 40 μm, more preferably between 1 and 30 μm, even more preferably between 2 and 25 μm.
 e) the average width of the valley is between 0-50 μm, preferably 0.5-40 μm, more preferably 2-20 μm, even more preferably 5-12 μm.

In addition, objects of the invention can be used to stimulate the early stage immune response to a foreign object to allow for a lowered end stage immune response, preferably minimizing the encapsulation tissue and inflammatory activity around a foreign object at the end stage. Topographies which can be used in this embodiments are of the type H/L, and can be defined by
 a) the average distance between adjacent protrusions is between 0-50 μm, preferably 0.5-40 μm, more preferably 5-30 μm, even more preferably 12.1-20 μm; and
 b) the top surface area of the protrusion is between 1 and 6000 μm$^2$, preferably 10 and 3000 μm$^2$, more preferably between 20 and 1000 μm$^2$, more preferably between 25 and 250 μm$^2$, even more preferably between 25 and 65 μm$^2$; and
 c) the protrusions cover between 3 and 90% of the surface part, preferably between 4 and 50%, more preferably between 5 and 30%, even more preferably between 5 and 10%

In addition, the length of a protrusion in a topography wherein the protrusions comprise only one protrusion element can be 0.01-100 μm, preferably, 0.5-50 μm, more preferably 1-50 μm, even more preferably 2-40 μm, and the length of a protrusion in a topography wherein the protrusions comprise multiple protrusion elements can be 0.01-100 μm, preferably 0.1-45 μm, more preferably 0.5-40 μm, even more preferably 1-30 μm.

The width of a protrusion in a topography wherein the protrusions comprise only one protrusion element can be 0.01-100 μm, preferably 0.5-50 μm, more preferably 1-50 μm, even more preferably 2-40 μm, and the width of a protrusion in a topography wherein the protrusions comprise multiple protrusion elements can be 0.01-100 μm, preferably 0.1-45 μm, more preferably 0.5-40 μm, even more preferably 1-30 μm.

Alternatively, an immunoregulating implant of the type H/L can be defined as an object having at least one topography wherein
 a) the valley wall height is 0.5-50 μm, preferably between 1 and 40 μm, more preferably between 2 and 35 μm, more preferably between 4 and 30 μm, and even more preferably between 5 and 28 μm.
 b) the valley wall profile is between 0 and 40 μm, preferably 0.1 and 35 μm, more preferably between 0.5 and 30 μm, even more preferably between 1 and 20 μm.
 c) the length of valley wall sections is 0.01-100 μm, preferably 0.1-50 μm, more preferably 1-40 μm, even more preferably 2-32 μm.
 d) the length of valley wall punctures is between 0 and 50 μm, preferably between 0.5 and 40 μm, more preferably between 1 and 30 μm, even more preferably between 2 and 25 μm.
 e) the average width of the valley is between 0-50 μm, preferably 0.5-40 μm, more preferably 5-30 μm, even more preferably 12.1-20 μm.

Immune cells, also known as white blood cells, are the cells of immune system that are in charge of defending the body against foreign objects including bacteria, viruses and other external objects such as biomaterials implanted in the body. These cells include macrophages, monocytes, B cells, T cells, megakaryocytes, basophils, neutrophils, eosinophils, dendritic cells, lymphocytes, mast cells, natural killer cells, foreign body giant cells (FBGCs) and other multinucleated cells. Immune cells can be found in blood or in the other tissues and may be obtained from different sources including human or animals, as is well known.

The (immune) response of the human body to foreign objects such as implanted biomaterials is called the foreign body response (FBR). Immune cells steer the foreign body response. A foreign body response may result in the formation of a capsule of fibrous tissue around the foreign object. This process known as encapsulation is the end-stage and chronic response of the inflammatory response to the foreign material and surrounding wounded tissue. While this process naturally occurs to defend the body and initiate the wound healing process, it may result in undesired impacts on implanted biomaterials and can compromise their function. Therefore, regulating the foreign body response to implanted biomaterials, or materials otherwise used in vivo, is an important issue in biomaterial design.

Several approaches have been developed for this purpose, which are mostly focused at the chemical level including change of the biomaterial design and the physicochemical properties of the biomaterial. Here is shown that by patterning the surface of a biomaterial with specific topographies, we can regulate (stimulate or down-regulate) the response of immune cells to the foreign object, independent of the chemistry of that biomaterial.

Any material may be used to make the object of the invention, as described above.

Modulation of immune cells includes affecting the morphology, stimulating or suppressing the attachment and proliferation, stimulating or suppressing the fusion of mononuclear cells into multinuclear cells, maintaining or changing the immune cell phenotype (differentiation of the cells), affecting the functionalities of immune cells, affecting the activation of the immune response, stimulating or preventing cell death, controlling the migration of the cells, and regulating the formation of fibrous capsule at the implantation site.

For example, suitable surface topographies are capable of modulating immune cell migration by stimulating or preventing the arrival of macrophages from blood to the tissue that surrounds the implantation site.

As another example, topographies can stimulate the attachment of macrophages to the foreign object and induce the fusion of the macrophages and formation of the FBGCs. Oppositely, other surface topographies prohibit the fusion of the macrophages and reduce the formation of FBGCs. Alternatively, macrophage attachment can be stimulated while FBGC formation is inhibited or vice versa.

Modulation of immunoregulation can be tracked by labeling of the immune cells attached to a surface or migrated to the implantation site and performing immunofluorescent staining followed by imaging techniques. Furthermore other techniques such as FACS may be used for detecting expressed surface markers in the immune cells, i.e. detecting the type of the cells. Furthermore, techniques such as immunofluorescent staining, qPCR, ELISA, western blot, microarray, histology, electron microscope imaging, etc. can be used for analyzing immune cell differentiation and biofunctioning.

Modulation of immune response can be also analyzed in vivo in various animal models such as mouse, rat, rabbit, etc. the implanted material and the surrounding tissue can be analyzed by (immune)histological techniques (immunofluorescent staining, colorimetric staining), electron microscope imaging, qPCR and RNA analysis, analysis of cytokine release, mechanical testing, etc.

Modulation of immune cells may be used in vitro as defined above, using culture-wares such as flasks, plates, bags, petri dishes, vessels, as well as in bioreactors, chips, (drug) screening platforms and/or biomolecule (vaccine/protein/antibody) production platforms.

In preferred embodiments, topographies have a strong impact on the response of monocytes/macrophages to polyurethane (PU) surfaces. Surface topographies can substantially affect the attachment of macrophages. The effect on the cells was not only limited to the number of the attached cells but also included changes in the morphological properties of the cells such as cell area. Furthermore, these surfaces affected the fusion of macrophages and therefore, strongly impacted the formation of foreign body giant cells. These effects were observed in an in vitro environment after 10 days of culturing monocytes on PU substrates featuring selected surface topographies. In vitro application of these immunoresponsive topographies include, but is not limited to, in vitro culture models to study or analyze the immune response or related physiology of cells, or as in vitro disease model. This early immune response is critical for implant acceptance and promotes acceptation of the implant in later stages of the immune response.

Preferably however, modulation of immune response is applied in vivo. Any long-term or chronically implanted device, including but not limited to, biosensors and bioelectrodes, cosmetic implants such as breast implants, bone implants such as ossicle bone implants, vascular implants (vascular artificial grafts, vascular access), dialysis access, cochlear implants and cardiovascular implants may be provided with a topography of the invention in order to modulate the immune response.

In vivo, topography-featuring PU substrates affected the early- and late-stage FBR in a subcutaneous mouse model. Different surfaces were able to induce a FBR ranging from very mild to strong. The infiltration of immune cells to the surrounding tissue (measure for the inflammatory activity level), presence of macrophages and formation of FBGCs, encapsulation of the implant at the interface and formation of a fibrotic capsule around the implants were some of the FBR-related parameters influenced by the presence of different surface topographies.

The thickness of the fibrous capsules around the PU implants varied upon introduction of different surface topographies at the surface of the implants. At the late (end) stage of the FBR, some surface topographies showed much lower amount of fibrotic encapsulation compared to the non-patterned control substrate and a silicon elastomer reference material, comparable or even lower than the empty wound (sham) where no foreign material was actually implanted. These surface topographies clearly reduce the immune response and prevent encapsulation of the implants which can result in improved functionality of the implant and improved patient outcome.

For the purpose of clarity and a concise description features are described herein as part of the same or separate embodiments, however, it will be appreciated that the scope of the invention may include embodiments having combinations of all or some of the features described. In particular, features described under the general description may be part of the specific embodiments.

The invention will now be illustrated by the following, non-limiting examples.

EXAMPLES

Materials and Methods for All Examples
Sample Fabrication

In the examples, metals and polymer substrates are used. For the full metal samples, i.e. Titanium (Ti) featuring individual topographies, the following procedure was applied to fabricate protrusions with 10 µm height:
1. Start with annealed Ti plates (99.6% purity), polished (roughness of about 0-0.01 µm) and cleaned.
2. Deposit 900 nm SiOx (plasma enhanced chemical vapor deposition, Oxford Plasmalab system 80), lithography (positive photoresist OIR 906-12, Arch Chemical, Inc) and hard bake (T=120° C., 60 sec).
3. Etch SiOx layer: directional reactive ion etching (Adixen AMS 100 SE) for 4.5 min with C4F8 flow of 20 sccm, He flow of 150 sccm, CH4 flow of 15 sccm, inductively coupled plasma (2800 W), capacitively coupled plasma (350 W) (T=−10° C., 2 min.).
4. Strip the photoresist with Oxygen plasma (Tepla 300E).
5. Etch Ti-substrate: alternate an etching step (combination of Cl2/BCl3/Ar plasma, 45 sec) and an oxidation step (O2 plasma, Oxford Plasmalab system 100, 15 sec; O2 flow of 30 sccm, ICP of 500 W, CCP of 15 W and 30 pressure of 33 mTorr).

For polymer substrates, for both substrates comprising a variety of different topographies and substrates holding one individual topography, the following procedure is followed:
1. Fabricate silicon wafers (mold) holding the inverse topography design through photolithography using a chromium mask.
2. Coat the silicon wafer with perfluorodecyltri-chlorosilane (FOTS, ABCR).
3. Optionally, replicate the topography design into intermediate molds of polydimethylsiloxane (PDMS Sylgard 184®, Dow Corning) and OrmoStamp (Micro Resist Technology GmbH).
4. Hot-emboss the topography into the polymer sample using the silicon wafers or intermediate molds (all samples demolding at 78° C.).
5. Optional: sputter coat with metal of interest.
6. O2 gas plasma (standard treatment for cell culture substrates).

TABLE 2

Materials and methods for topography-featuring substrate fabrication

| Example | Material | Specifics, fabrication parameters |
| --- | --- | --- |
| 1-4 | Polystyrene (PS; 190 µm thick, GoodFellow) | Hot embossing: 140° C., 10 bar, 5 min. |
| 5 | Titanium-coated Polylactic acid (PLA; 250 µm thick, Folienwerk Wolfen GmbH) | Hot embossing: 120° C., 40 bar, 5 min. Surface treatment: Ti-sputter coating (200 nm). |
| 6-7 | Polyurethane (PU; Bionate 55D PCU, DSM Biomedical Inc.) | Hot embossing: 140° C., 10 bar, 5 min. For exp. 7: two identical molds were used at both sides of the samples to embed the topography into both sides (size 4(l)*10(w)*0.15(d), in mm), sterilization through autoclaving |

Cell Culture and Analysis

For the in vitro examples, cells of interest were cultured on substrates adapted to allow comparison between various topographies, as well as on substrates holding one individual topography. The following procedures are followed;
1. Sterilize (70% ethanol) and wet the substrate (cell culture medium, min. 24 hours)
2. Optional: collagen coating with fresh 20 µg/ml collagen I (rat-tail, VWR) in 0.02M acetic acid, 100 µl/well, 1 hr. incubation at room temperature and washed 3× with PBS
3. Seed the desired cells (for details, see table 3) and maintain the cultures at 37° C. in 5% $CO_2$ with medium being refreshed every 2-3 days:

TABLE 3

Conditions for the in vitro cell culture experiments

| Example | Cell type | Seeding density (cells/cm$^2$) | Cell culture medium |
| --- | --- | --- | --- |
| 1-2 | Rhesus monkey-derived hepatocytes | 280.000 | William's E + Glutamax (Invitrogen), FBS, 1% NEAA, pen/strep, 1% insulin/transferrin/selenium, 1% Na-pyruvate, 50 µM β-mercapto-ethanol, $10^{-7}$ M hydrocortisone |
| 3-4 | Primary human hepatocytes (PHH) | 192.000 | William's E + HepaRG + Glutamax (Invitrogen) |
| 5 | Human mesenchymal stromal cells (hMSCs) | multiple comparison: 3.000 Validation: 3.500 | αMEM (Gibco), FBS, L-glu, AsAc, pen/strep |

TABLE 3-continued

Conditions for the in vitro cell culture experiments

| Example | Cell type | Seeding density (cells/cm$^2$) | Cell culture medium |
|---|---|---|---|
| 6 | Human monocytes freshly isolated from whole blood using a Percoll-Ficoll protocol* | 600.000 | Macrophage-SFM (Gibco) + 2X FBS (Sigma-Aldrich), pen/strep |

FBS = 10% fetal bovine serum (Lonza), l-glu = 2 mM l-glutamine (Gibco), AsAc = 0.2 mM ascorbic acid (Sigma Aldrich), pen/strep = 100 U ml$^{-1}$ penicillin and 100 g ml$^{-1}$ streptomycin (Gibco).
*protocol described here: Repnik U et al. *Journal of immunological methods* 2003; 278 (1-2): 283-292.

4. After harvesting, fixate the samples with Paraformaldehyde 4% and fluorescently label the cells (details see Table 4);

TABLE 4

Immunofluorescent labels used for the in vitro experiments

| Example | Time point (days) | Labels |
|---|---|---|
| 1 | 31 | Primary mouse anti-human CD81 antibody (BD Pharmingen) and goat anti-mouse AF488 IgG (Invitrogen), DAPI (cell nuclei, Sigma Aldrich) |
| 2 | 14 and 30 | Primary mouse anti-human CD81 antibody (BD Pharmingen) and goat anti-mouse AF488 IgG (Invitrogen), DAPI (Sigma Aldrich) |
| 5 | 4 | Primary human alkalinephosphatase (ALP, Santa Cruz), goat anti-mouse AF 594 (Invitrogen), Phalloidin (cytoskeleton, Invitrogen), DAPI (Sigma Aldrich). |
| 6 | 10 | Mouse anti-human CD14 antibody (Santa Cruz), secondary goat anti-mouse AF488 antibody (Invitrogen), CellMask ™ Orange (Molecular Probes), Phalloidin-AF594 (Invitrogen) and DAPI (Sigma-Aldrich) |

5. (I) Image the comparative topographies using an automated slide scanner capturing images of each individual TopoUnit, or (II) capture 10 randomly-selected images for topography-featuring substrates. Asses the images obtained for both proper culture quality (number of cells, distribution) and image quality.
6. Analyze the images using MATLAB scripts and CellProfiler [Carpenter AE et al. Genome Biology 2006; 7: R100, Hulsman M et al. Acta Biomaterialia 2015; 5(15): 29, Unadkat H et al. PNAS 2011, 108: 16565] (analysis parameters details see Table 5).

TABLE 5

Analysis parameters

| Example | Analysis parameters |
|---|---|
| 1-2 | Number of attached cells, surface area covered by the cells, and CD81 integrated intensity (average CD81 intensity per cell, indicative for hepatocyte phenotype). |
| 5 | Mean ALP intensity per cell, integrated (total) ALP intensity per cell, and relative integrated ALP intensity (integrated ALP intensity normalized for integrated cytoskeleton intensity). |
| 6 | Number of attached cells, number of multinuclear cells, average number of nuclei per cell, multi-nucleation and cell area. |

7. In vitro validation and secondary screening, using various methods:
Malaria-infection (example 2): add 50000 Plasmodium Cynomolgi sporozoites/well (in 130 µl) at day 2 and include HSP70 (Heat shock protein 70) during labeling to visualize the P. sporozoites. Quantify the number of the infected cells manually and calculate the infection efficiency (infected cells/total number of cells).
qPCR (examples 3-4): isolate mRNA using the Trisol protocol, i.e. lyse the cells in Trisol and purify the lysate containing the mRNA. Pool the lysate of 2 replicates and perform 3 measurements per pool (6 biological replicates). Synthezise the isolated RNA into cDNA using an iScript kit (Bio-Rad) according to the manufacturer's protocol and dilute in water for quantitative real-time PCR (qPCR, Bio-Rad) using Sybr green I master mix (Invitrogen) and primers (Sigma) for the specific genes (Table 6). Gene expression was normalized to housekeeping gene GAPDH levels (ΔCT method) and subsequently normalized to the level of the same markers in the collagen sandwich at day 3 presenting fold inductions (ΔΔCT method).

TABLE 6

Details of analyzed genes

| Example | Housekeeping gene | Analysis parameters |
|---|---|---|
| 3 | GAPDH | HNF4α, Albumin and Cyp3A4 |
| 4 | GAPDH | HNF4α, Albumin, Cyp3A4, Cyp2C9, Cyp1A2, E-cadherin |

8. In vivo validation, using various animal models
Rabbit Femur-Model for Validating Osseo-Integration Example 5

Full Titanium topography-featuring samples (coin-shaped, 6.25 mm diameter, 1.95 mm thick), together with controls, were implanted 24 New Zealand White female rabbits to assess new bone formation and osseointegration. The samples were first cleaned ultrasonically in acetone for 1 h and in IPA for 1 h and sterilized using autoclave. The animal study procedures were approved by the local ethic committee.

Implantation was performed under general anesthesia and sterile conditions. After sedation by intravenous application of pentobarbital sodium (3.0 mg/kg body weight), the animals were shaved at the operation site and sterilized with iodine and 70% ethanol (EtOH). On the proximal part of the femur, a 5 cm incision was made till the underlying periosteum was exposed and also through the periosteum. The periosteum was removed from the surface. Two holes were drilled and the implants were placed in the holes and kept in place by a mesh plate. The subcutaneous layers were repositioned and sutured with 4-0 silk suture. The animals were sacrificed after 4 or 8 weeks and the femur with implant was removed. The explanted samples were then fixated in 10% neutral buffered formalin and kept at 70% EtOH for further analysis/characterization.

Analysis was performed through (1) Pull-out tensile testing using a mechanical pull bench: the pulling force was applied to the samples with the speed of 1 mm/min until the implant was detached from the bone while recording all forces applied; and (2) Histology: fixed samples were dehydrated in ethanol series and embedded in methyl methacrylate (MMA). Histological sections were made and stained with 1% Methylene Blue and 0,3% Basic Fuchsin solution. 3 Sections per samples were scanned and the bone-to-implant contact percentage (% BIC) was measured (defined as all areas with direct bone contact to the implant without gaps or fibrous tissue).

Mouse Subcutaneous-Model for Validating Immune-Regulation

Example 7

Polyurethane (PU) implants, together with controls, were implanted in 64 female mice (Harlan, approx. 9 month old, weight of 18-20 g, 4 mice with 2 identical implants (n=8) per condition) to assess the mice' immune response. Non-patterned (NP) implants, empty wounds (sham group) and silicon elastomer controls (SE, halved catheters of a diameter of 2.5 mm and a thickness of 0.6 mm, Medtronic Medical) were included as controls. The study was performed under proper and ethically approved protocols by Dutch law.

Implantation was performed under general anesthesia and sterile conditions. After sedation by 2% isoflurane (Pharmachemie) in oxygen in a laminar flow cabinet, followed by a subcutaneous injection of buprenorphine (Temgesic, RB Pharmaceuticals Limited, 0.05 mg/kg) 15 min prior to the surgical procedure for pain control, the backs of the mice were shaved and disinfected with 70% ethanol. On each side of the animals back, an incision of 0.4 cm was made 1 cm lateral to the spine. Subsequently, the 1 cm long implants were placed subcutaneously with minimal tissue damage using a sterile tweezers. The incisions were then closed. The sham group and SE controls were implanted similarly. After surgery, the mice were housed individually until the wounds healed. Subsequently, the animals were housed in pairs until end of the study. 9 or 60 days after the study, indicative for the early and later stage immune response respectively, the animals were sacrificed according to ethically approved protocols and the samples together with the subcutaneous tissue and connected skin were harvested. Half of each biopsy was fixed in 4% paraformaldehyde followed by methyl methacrylate/butyl methacrylate (MMA/MBA, Merck), 3 μm section were cut, deplastified in acetone and washed in demineralized water. Per biopsy, 3 consecutive sections were either stained with hematoxylene and eosin (H&E), Picro-sirius red (PSR) or F4/80.

The H&E staining (for nuclei and cell cytoplasm staining) requires incubating the slides in hematoxylin for 5 minutes followed by 5 minutes washing in water and counterstaining by eosin and again washing. Next, the slides were incubated in ethanol and xyleen for dehydration and mounted on a cover slip using Vectamount (vector labs).

For PSR (for visualization of collagen and collagen-rich tissues) requires incubating the slides in PSR solution (Klinipath) for 20 minutes, washing with 0.1 N HCl and dehydrating in ethanol and xyleen. Mounted was performed as explained above.

F4/80 (a protein marker of macrophage populations) requires incubation in methanol with 0.3% $H_2O_2$ for 20 min in dark, washing with water, incubating in 50 mM Tris, 0.9% NaCl buffered saline (TBS), again washing with water, followed by incubating with Superblock (Klinipath) for 10 minutes, then with rat anti-mouse monoclonal F4/80 antibody (Serotec, 1:1000 in TBS) overnight, with rabbit anti-rat igG antibody (SBA/ITK, 1:3000 in TBS and 20% normal mouse serum) for 30 minutes, BrightVision anti rabbit AP antibody (Immunologic) for 30 minutes and finally with Vector blue (Vector Labs) for 10 minutes. The slides were then washed with TBS, then with tap water, stained with hematoxylin for 1 minute and again washed with tap water. After drying, the slides were mounted, and then scanned, imaged and analyzed (digital pathology software, IntelliSite, Philips).

The slide were scored from 0 to 3 (0=none, 1=mild, 2=moderate and 3=sever) for the infiltration of the immune cells, formation of FBGCs, encapsulation of the implant and formation of fibrous tissue around the implant. The thickness of the fibrous connective tissue around the implants was measured at 6 random sites around the implants. The scoring and measurement of the thickness of fibrous layer was performed blinded by two persons separately.

Figure 14:
FIG. 14 illustrates unit cell and protrusion design parameters and performance of topographies to maintain hepatocytes functionality in long-duration cultures. Protrusion shape: white indicates the top surface area, black indicates the valley surface. Geometrical parameters are based on calculations. Nonpatterned (NP) sample and a selection of 'basic topographies' (circles, triangles and rectangles) are included as controls.
Figure 14:
Figure 14:
Figure 14:
Figure 14:
Figure 14:
Figure 14:
Figure 14:
Figure 14:
Figure 14:
Figure 14:
Figure 14:
Figure 14:

Example #1: Surface Topographies to Maintain Primary Rhesus Macaques-Derived Hepatocytes in Culture FIG. 14 shows topographies capable to maintain and increase functionality of hepatocytes in culture (H1-10), the geometric shape and the performance for the analyzed parameters when made into polystyrene. As controls, the performance of nonpatterned (NP) substrates (also polystyrene) as well as a selection of more 'basic' designed topographies (triangles, B1-2) are included. Low cell numbers indicate low attachment and/or low cell survival, whereas high cell numbers (>60) are undesirable as these cells do not express proper hepatocyte morphology and phenotype. Therefore, medium number of cell levels indicate the best performance (40-60), especially when combined with proper surface coverage and cell morphology (judged by eye upon selecting hit-topographies).

Topographies H1-H10 have medium number of attached cells (44-60) combined with 29-36% of cell coverage. In contrast, the NP substrate has medium number of cells attached, leaning towards to low end (44) combined with lower cell coverage (27%). However, most prominent on NP substrates is the poor cell morphology and loss in phenotype, which correlates to the poor results after prolonged culture times (see image FIG. 2*c,* 31 days of culture). Basic topographies result in either low cell number combined with low cell coverage (no proper hepatocyte culture is maintained) or in high cell number and/or cell coverage (non-functional and even non-phenotypical hepatocytes). B1, with a protrusion coverage of 36% (above the range for best performing topographies of 8-35%), results in high cell number (73) with average cell coverage (35%) indicating these cells are small, not well-spread and not presenting the proper morphology and therewith not having the phenotype and functionality. B2, with a protrusion coverage of 7% (below the range for best performing topographies), results in low cell number (35) with low cell coverage (22%) indicating no proper hepatocyte culture.

Validation of the Topographies

Validation confirmed the efficacy of the topographies in supporting in vitro culture of hepatocytes. While regular tissue culture polystyrene (TCPS) support hepatocytes for less than 5 days, TCPS with collagen-coating up to 10-14 days, our best performing topographies (with and without collagen coating) support hepatocytes for up to 31 days.

Figure 2:
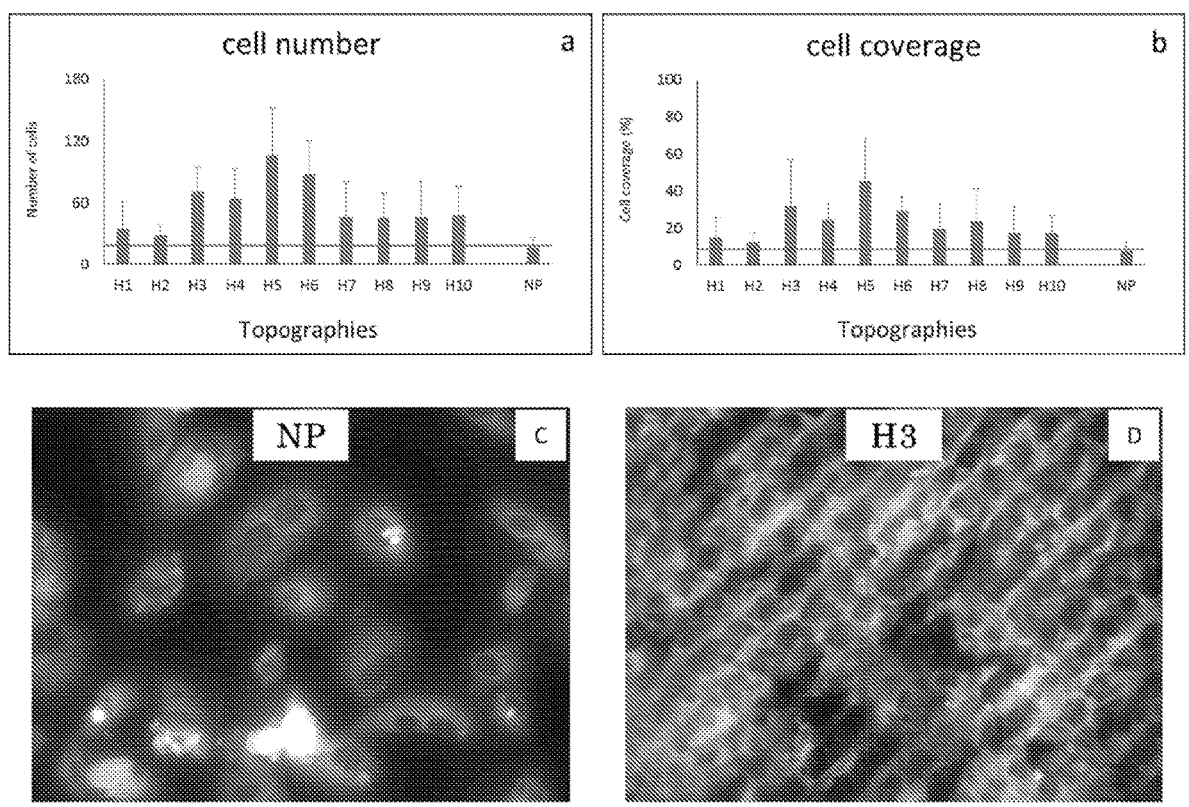
FIG. 2: Topographies H1-H10 affect Rhesus monkey-derived hepatocytes in culture. Analyzed for (a) the number of attached cells within the analyzed sections and (b) the surface area covered by cells. Visualization of cells cultured on (c) nonpatterned (NP) substrates and (d) substrates featuring topography H3. Conditions: all substrates without collagen coating, 31 days of culture, NP as control which level is indicated by the red line.

All 10 topographies strongly promote in vitro culture of hepatocytes. The topography-featuring substrates have 2-6 times more cells attached to the surface after 31 days of culture compared to the nonpatterned control surface (FIG. 2a), and were confirmed to be CD81-positive and thus to be hepatocytes. Also, the cells cover 2-5 times more surface area of the topography-featuring surfaces compared to the nonpatterned control surface (FIG. 2b). Finally, hepatocytes cultured on the topography-featuring substrates possess cell morphology much more similar to the in vivo (natural) organization and morphology of hepatocytes in the liver (H3, FIG. 2d), strongly contrasting hepatocyte morphology seen on non-patterned control substrates (FIG. 2c).

Secondary Screening of Topographies

The best performing topographies (H3, H4, H5, H6, H8) in experiment 1 were further validated. Besides the 31-day validation also day 8 was included, for comparison to the current standard of culturing maximally 8 days. Also, part of the samples were infected with the malaria parasite to prove the hepatocyte functionality (malaria parasites can only infect functional hepatocytes).

Again, screening and validation results were confirmed showing high number of cells, high cell coverage (FIG. 3a, b, d and e) and proper expression of CD81.

Figure 3:
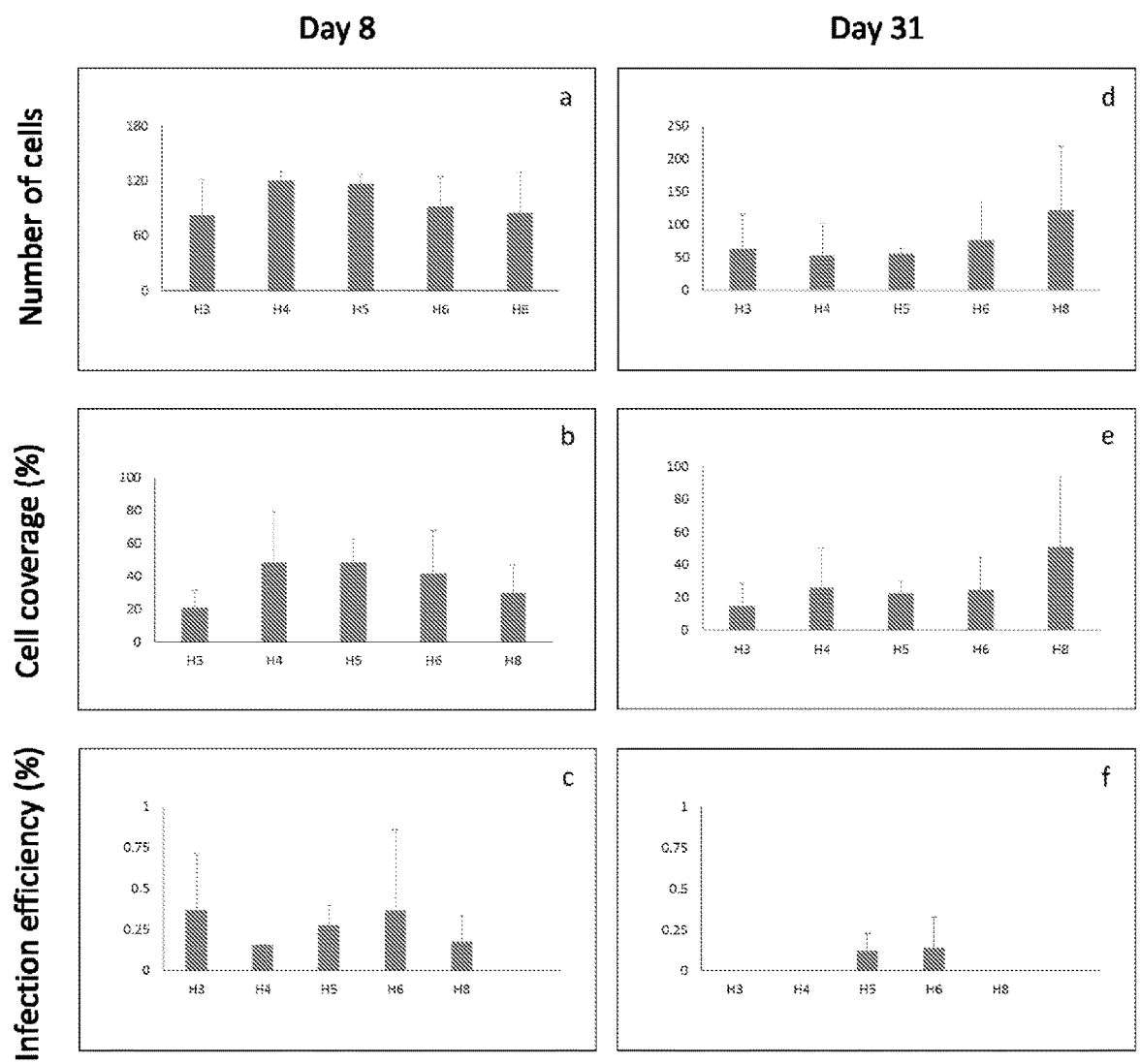
FIG. 3: Topographies H3, H4, H5, H6 and H8 affect Rhesus monkey-derived hepatocytes in culture. Analyzed for (a, d) the total number of attached cells within the analyzed sections, (b, e) the surface area covered by cells and (c, f) the malaria parasite infection efficiency after (a-c) 8 and (d-f) 31 days. Conditions: all substrates without collagen coating.

Infection efficiency on the topography-featuring substrates was up to 0.5% at day 8 and still up to 0.15% at day 31 (FIG. 3c, f). These infection levels are in line with regular levels using nonpatterned collagen-coated surfaces (day 8). Levels at day 31 cannot be compared since hepatocytes cannot be cultured beyond 10-14 days on nonpatterned (collagen-coated) surfaces. The fact, however, that the *plasmodium* sporozoites are still detected at day 31 is unprecedented and is a unique benefit of the topographies by itself bringing great opportunities in anti-malaria drug R&D.

Conclusions

The identified surface topographies promote, without the need of collagen, hepatocyte attachment and support their in vitro culture for 31 days while expressing the hepatocyte phenotype, even in the presence of malaria parasites. In strong contrast, current standard methods only allow in vitro culture for up to 8-11 days and require collagen. The best performing surface topographies to support hepatocytes in culture have protrusions with a top surface area of 20-250 $\mu m^2$, surface coverage of 8-35% and average distance between protrusions of 3-25 $\mu m$.

Example #2: Surface Topographies to Maintain Primary Human-Derived Hepatocytes in Culture The topographies, with and without collagen-coating, were validated for supporting prolonged in nitro culture of primary human-derived hepatocytes (PHH). The gold standard 'collagen-sandwich' (CS), where the hepatocytes are cultured between two layers of collagen, is included as benchmark (up to 14 days) and nonpatterned (NP) surfaces as controls.

Results

Figure 4:
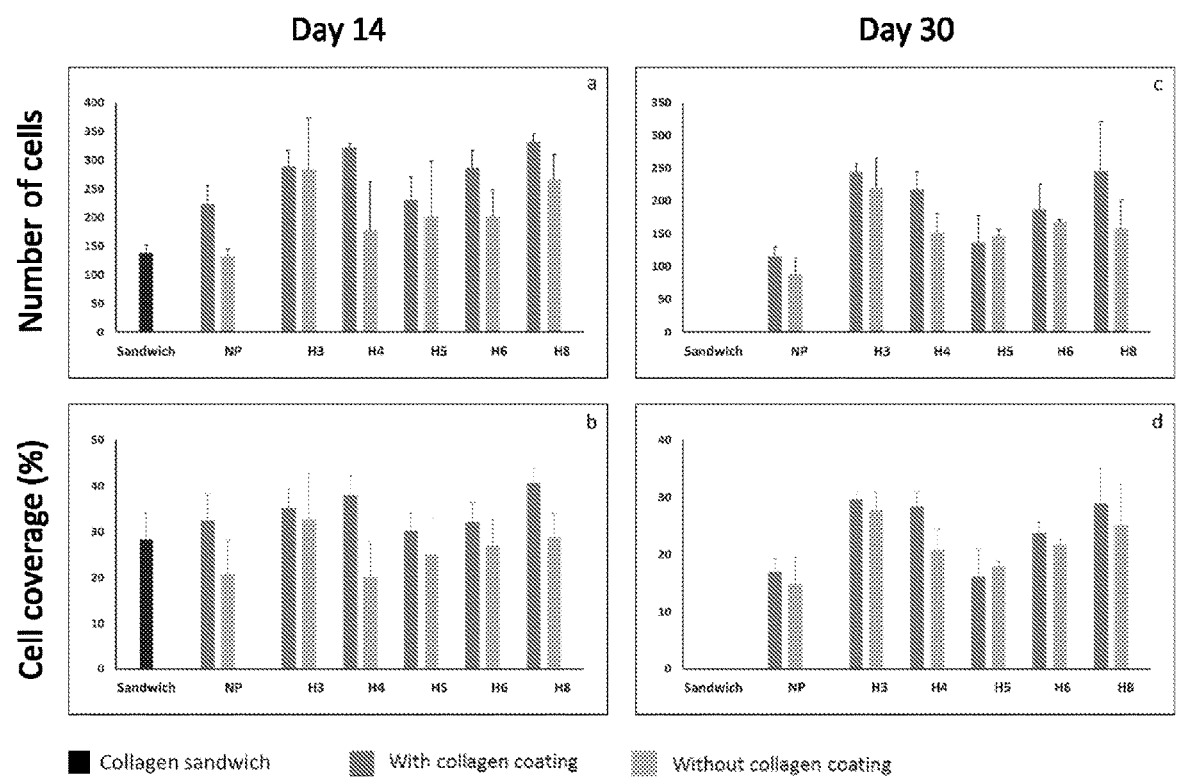
FIG. 4: Topographies H3, H4, H5, H6 and 118 affect primary human-derived hepatocytes (PHH) in culture. Analyzed for (a, c) the total number of cells attached within the analyzed sections and (b, d) surface area covered by cells after (a, b) 14 and (c, d) 30 days of culture. Conditions: all substrates with and without collagen coating including NP (control), collagen sandwich included as benchmark.

All topography-featuring substrates outperformed the nonpatterned controls, both with and without collagen, and at both time points. Both at day 14 (FIG. 4a, b) and day 30 (FIG. 4c, d), the total number of cells and coverage of the surface was higher on the topography-featuring substrates than the CS (day 14 only) and nonpatterned controls, even significantly more so at day 30. However, the most striking effects were seen in cell morphology. On certain topographies the cells showed a clear resemblance to the natural (in vivo) liver organization and morphology whereas at other topographies and the nonpatterned controls the cells did not show such organization and cell shape. Coating the topography-featuring surfaces with collagen did not affect the results much.

Conclusions

The topographies of the invention showed excellent performance for prolonging proper in vitro culture of PHH for one month while the current gold standard CS only allows for a maximum 2 weeks, and in practice can only be used for 8 days. The best performing surface topographies for supporting hepatocyte cultures have protrusions with a top surface area of 20-250 $\mu m^2$, surface coverage of 8-35% and average distance between protrusions of 3-25 $\mu m$.

Example #3: Surface Topographies to Maintain Primary Human-Derived Hepatocytes Functional The most promising topographies (H3, H4 and H8, with and without collagen coating) of examples #1-2 are analyzed for expression of PHHs hepatocyte-specific phenotype, indicative for functionality, during two-weeks of in vitro culture. CS and NP surfaces are included as controls. Gene expression levels (all normalized for CS day 3 levels) on topography-featuring surfaces at day 14 are compared to CS levels at both day 14 and day 3.

Results

Figure 5:
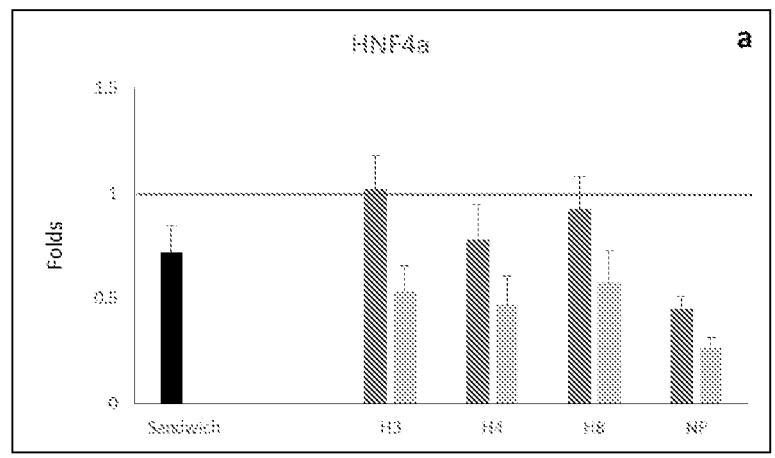
FIG. 5. Topographies H3, H4 and H8 affect primary human-derived hepatocytes (PHH) in culture. Analyzed for biomarkers of hepatocyte functions including (a) HNF4a, (b) Albumin and (c) Cyp3A4 at mRNA level after 14 days. Conditions: all substrates with and without collagen coating including NP (control), collagen sandwich included as benchmark. The red line indicates the level of expressed markers in the collagen sandwich at day 3 (set to 1) and is used to normalize all other samples to (fold induction).
Figure 5:
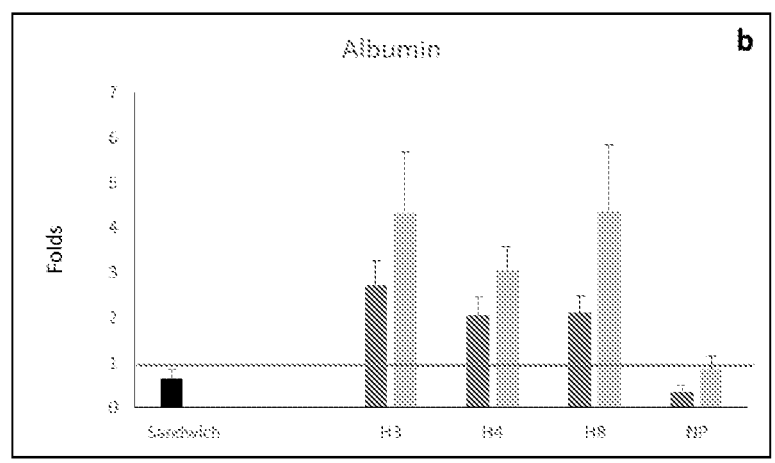
Figure 5:
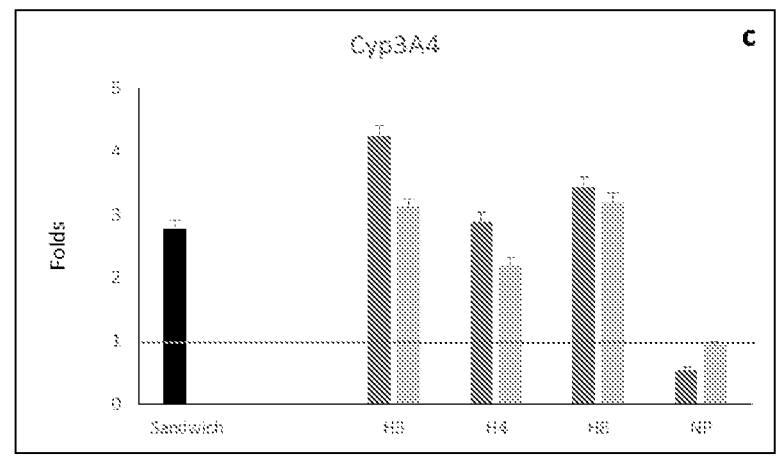

HNF4a (FIG. 5a, involved in transcription of hepatocyte specific proteins and in regulating hepatocyte functions) is expressed higher on all topography-featuring substrates with collagen coating compared to the CS at 14 days, and even at the level of the CS at day 3.

Albumin (FIG. 5b, an indicator of hepatocyte metabolism) is expressed substantially higher (up to over 4 times) in all topography-featuring substrates, with and without collagen coating, compared to the CS at both time points, revealing the efficiency of the surface topographies in maintaining and perhaps even enhancing the metabolic-related phenotype in long term in vitro culture.

Cyp3A4 (FIG. 5c, an important detoxification marker) is expressed much higher (up to 4 times) in all topography-featuring substrates, with and without collagen, compared to the CS at both time points indicating improvement of this function-related phenotype by applying these surface topographies.

Expression of other Cyp-markers (a.o. Cyp2B6, Cyp1A2, Cyp2C9, involved in detoxification) on the topography-featuring surfaces was higher than (Cyp2B6 and Cyp1A2) or similar to (Cyp2C9) the CS (at day 14).

For CD81and E-cadherin (involved in cell adhesion, formation of tight junctions and cell-cell communication), expression levels on the topography-featuring surfaces was comparable to the CS, and higher compared to NP at day 14.

Conclusion

The topographies were able to maintain the hepatocyte phenotype for prolonged periods of time, comparable with the current gold standard at early time points. In some cases, functionality even increased during 14 days of in vitro culture. The best performing surface topographies to support hepatocyte cultures have protrusions with a top surface area of 20-250 μm², surface coverage of 8-35% and average distance between protrusions of 3-25 μm.

Example #4: Surface Topographies to Maintain Primary Human-Derived Hepatocytes Functional in Long-Term Cultures The most promising topography (H3) of examples #1-3, with and without collagen, is analyzed for its effect on PHHs maintaining or even regaining their phenotype during a 24 days culture period. Genes analyzed similar to example 3. CS (up to day 14) and NP controls are included.

Results

Figure 6:
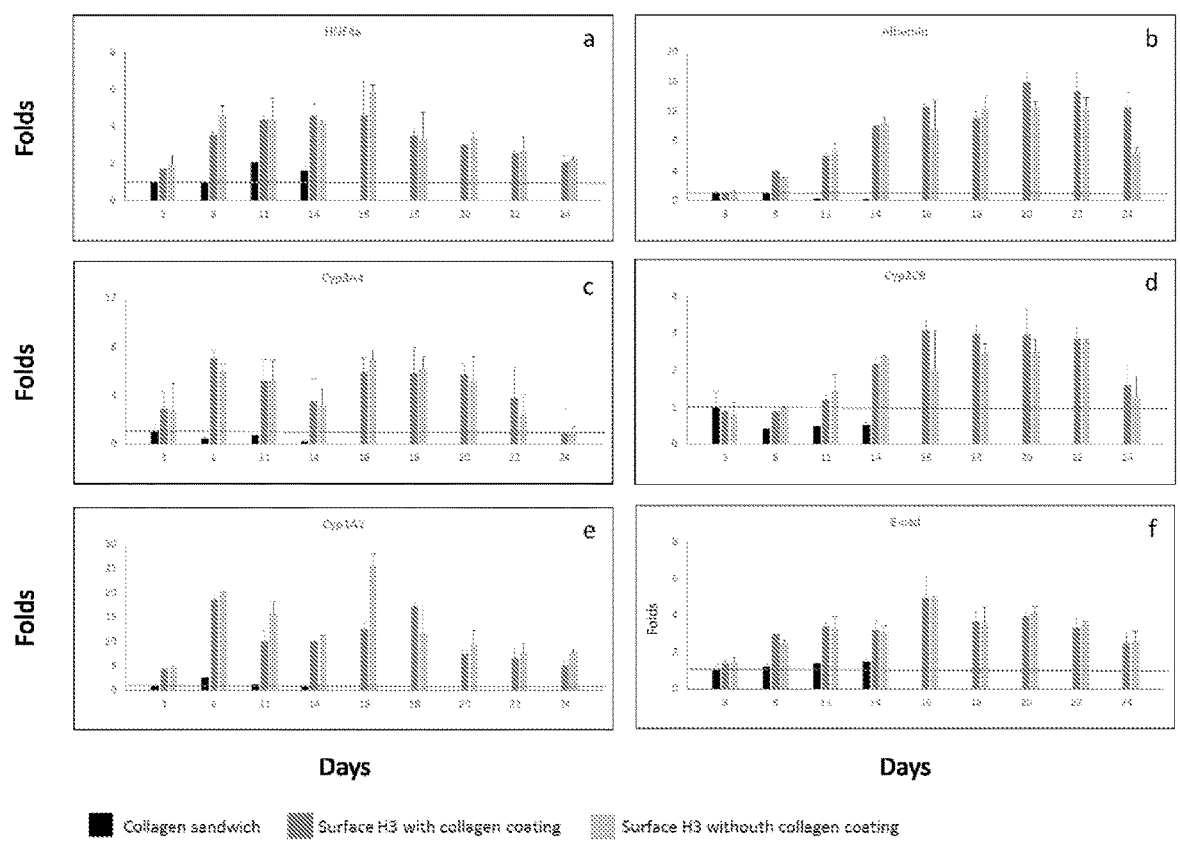
FIG. 6. Topography H3 affect human-derived hepatocytes (PHH) in culture. Analyzed for biomarkers of hepatocyte functions including (a) HNF4a, (b) Albumin and (c) Cyp3A4, (d) Cyp2C9, (e) Cyp1A2 and (f) E-cadherin (E-cad) for up to 24 days. Conditions: all substrates with and without collagen coating including NP (control), collagen sandwich included as benchmark. The red line indicates the level of expressed markers in the collagen sandwich at day 3 (set to 1) and is used to normalize all other samples to (fold induction).

On H3-surfaces, with and without collagen coating, all analyzed genes (FIG. 6) were expressed substantially higher for all time points (between day 8-24) compared to the levels at day 3, which is considered to be the time the cells need to recover to the normal hepatocyte state. In sharp contrast, the expression of all biomarkers in the CS are at best maintained at the same levels as at day 3 or are reduced to (much) lower levels in time (max. 14 days). Comparing H3-surfaces to CS directly, at day 24 all genes are still expressed at similar or even (much) higher levels on H3 than the CS at both day 8 (gold standard) and even day 3.

Conclusion

PS substrates featuring surface topography H3 were not only able to maintain the hepatocyte phenotype and functionality compared to the current gold standard, but they even enhanced these functions including metabolic activity, signaling, protein secretion and detoxification and enable prolonged in vitro culture to at least 24 days (compared to currently 8 days for the gold standard). The surface topographies that perform the best in supporting hepatocyte cultures have protrusions with a top surface area of 20-250 μm², surface coverage of 8-35% and average distance between protrusions of 3-25 μm.

Example #5: Surface Topographies to Enhance Osseointegration and Fixation of Bone/Dental Implants A titanium-coated chip with various different topographies was used to study surface topographies which improve osteogenic differentiation of human mesenchymal stromal cells (hMSCs) to stimulate new bone formation with the goal to improve osseointegration and fixation of orthopedic and dental implants into bone. When hMSCs differentiate into the osteogenic lineage and form new bone, they express the osteogenic marker ALP and was therefore use as marker.

In Vitro Validation of Topographies

The topographies that stimulated ALP expression according to a combination of parameters described in Table 5, were selected as hit-topographies FIG. 15, O1-O10). The ALP expression on the topographies O1-10 range for the integrated ALP intensity (iALP) from nearly 600 to over 1000 and for the relative integrated ALP intensity (riALP) from 36 to 58. In strong contrast, the nonpatterned (NP) control substrates values 14 (iALP) and 212 (riALP) and for basic topographies (triangles and rectangles, B3-5) the values range between 14-19 (iALP) and between nearly 350 to just over 500 (riALP). These basic topographies have a protrusion surface coverage well below the range for best performing topographies (4-25% vs. 30-65%) and also the protrusion top surface area is below the range for best performing topographies (25-29 μm² vs. 30-750 μm²). This data indicates the superiority of surface topographies O1-O10 in stimulating ALP expression and thus osteogenesis.

Validation of these hit-surfaces using well-known in vitro technique, including protein expression (FACS), gene expression (qPCR) and mineralization (tetracyclin staining) confirmed the efficacy of the hit-topographies and their superior performance compared to NP surfaces.

In Vivo Validation of Topographies

The best performing topographies of the in vitro experiments were manufactured into full-body titanium and implanted in vivo in a rabbit femur model assess their osseointegration potential at 4 and 8 weeks. NP controls were included in this study for comparison.

Figure 7:
FIG. 7a, b: 2 Typical images of histological sections of titanium implants featuring two different topographies selected for their osteogenic properties in contact with bone tissue after 8 weeks of implantation.
Figure 7:
Figure 8:
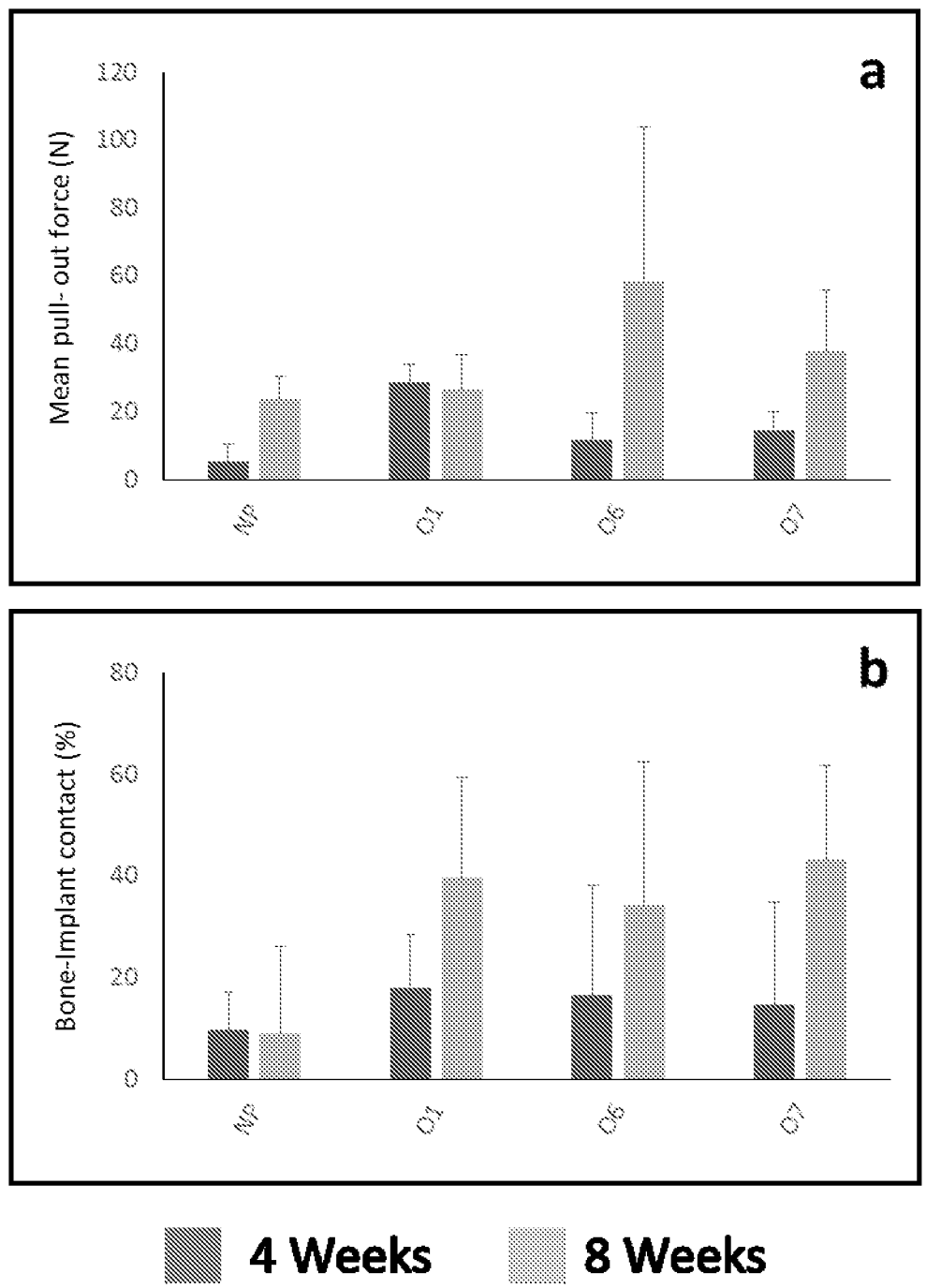
FIG. 8: Topographies O1, O6 an O7 affect osteogenic properties in vivo. Analyzed for (a) pull-out force required to detach implants from bone and (b) percentage of the implant surface in direct contact with bone. Conditions: 4 and 8 weeks of implantation in rabbits, implants featuring topographies O1, O6 and O7, controls included nonpatterned implants.

Both the mechanical and histological analysis (FIG. 7) revealed the topographies-featuring implants stimulate new bone tissue formation. The pull-out test (FIG. 8a) shows that the NP controls have the lowest level of osseointegration after both 4 and 8 weeks. At 4 weeks, all implants featuring one of the hit-topographies require between 2-4 times the pull-out force of the NP control, with one hit-topography-featuring implant standing out requiring over 5 times. At 8 weeks, the NP control still requires less force to be detached compared to the best scoring topography at 4 weeks. The hit-topography-featuring implants require about 2 times the force of the NP control, with one topography standing requiring over 3 times.

The histological bone-to-implant (BIC) contact analysis (FIG. 8b) shows the NP control has low BIC of around 10% at both 4 and 8 weeks. The topography-featuring implants show much higher BIC at both time points, even though high between-animal variation is observed. The results show up to 80% BIC for the hit-topography featuring implants at 8 weeks.

These results provide demonstration of the effectiveness of the hit-topographies to induce osseointegration in a relevant in vivo model.

Conclusion

The identified topographies possess highly enhanced osseointegration properties compared to nonpatterned control implants. The results furthermore show that the topographies of the invention with a regular pattern of protrusions/valleys provide better osseointegration than a clinically-applied benchmark having a randomly roughened surface. Thus, the topographies of the invention display increased fixation and increased bone formation, relative to known implants.

The best performing surface topographies stimulating osteogenesis have protrusions with a top surface area of 30-750 μm², preferably 150-450 μm², surface coverage of 30-65%, preferably 35-60% and average distance between protrusions of 2-25 μm, preferably 5-15 μm.

Example #6: Surface Topographies to Regulate the Immune Response, In Vitro

Surface topographies which regulate the response of immune cells to biomaterials were identified using topographies made from polyurethane. Upon implantation of a biomaterial into body, an immune response is triggered in which the body attempts to heal the wounded tissue surrounding the biomaterial and to remove/isolate the foreign biomaterial. This response is called the foreign body response (FBR). The first, acute response is important for the acceptance of the biomaterials but may continue into a chronic inflammation process including excess formation of the fibrotic capsule around the implant. Therefore, we use the FBR, and specifically the associated formation of foreign body giant cells (FBGC, multi-nucleated cells), as marker.

Surface topographies with ability to regulate the FBR were selected and embedded into scaled-up substrates (of 2 cm² surface area) and validated, using 1 donor.

Secondary screening, with 2 donors, included a more complex, mixed population of mononuclear cells (including monocytes) by eliminating the Ficoll-gradient during isolation in order to better mimic the in vino environment for the short stages of the immune response. Nonpatterned (NP) substrates were included as controls.

In Vitro Validation of Topographies

The topographies that most strongly affect macrophage attachment and fusion into FBGCs, assessed by a combination of parameters described in Table 5, were selected as hit-topographies (FIG. 16, I1-I3). The topographies can both stimulate and suppress macrophage attachment and fusion in vitro. Stimulating topographies (I1-4) result in high number of macrophages (12-15) with high multi-nucleation (12-16), while suppressing topographies (I5-13) have low macrophage attachment (3-6) and low multi-nucleation (4-5). In contrast, NP and basic topographies (circles and triangles, B6-7) induce moderate effects on both macrophage attachment (NP: 6, B6-7: 8-10) and on multi-nucleation (NP: 5, B6-7: 7-10) and will not allow control over the immune response. B6 has a protrusion top surface area below the ranges for all three groups of best performing topographies (19 µm² vs. 20 µm² and over) while B7 has a surface coverage outside of the ranges for all three groups of best performing topographies (13% vs. 15-25% H/H, 5-10% H/L and 26-50% L/L).

Figure 9:
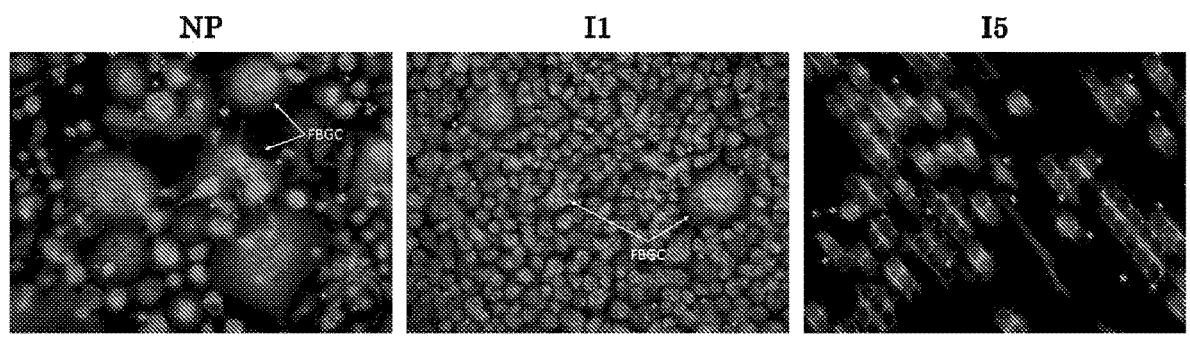
FIG. 9. Topographies affect macrophage attachment and foreign body giant cell formation in vitro. Typical images show the effect of topography I1 (middle) and I5 (right) versus the nonpatterned substrate (left, control) at day 10. The arrows indicate foreign body giant cells (FBGC).

Validation of these surface topographies confirms the efficacy of the topographies to regulate the immune response greatly. To illustrate, FIG. 9 shows early stage in vitro macrophage attachment and FBGC formation on topography-featuring surfaces (I1 and I5) compared to the NP surface; Surface I5 has low macrophage attachment and fusion while surface I1 has high macrophage attachment and FBGC formation indicating an intense FBR. NP shows lower number of attached cells compared to macrophages however, several multinuclear cells are formed.

Figure 10:
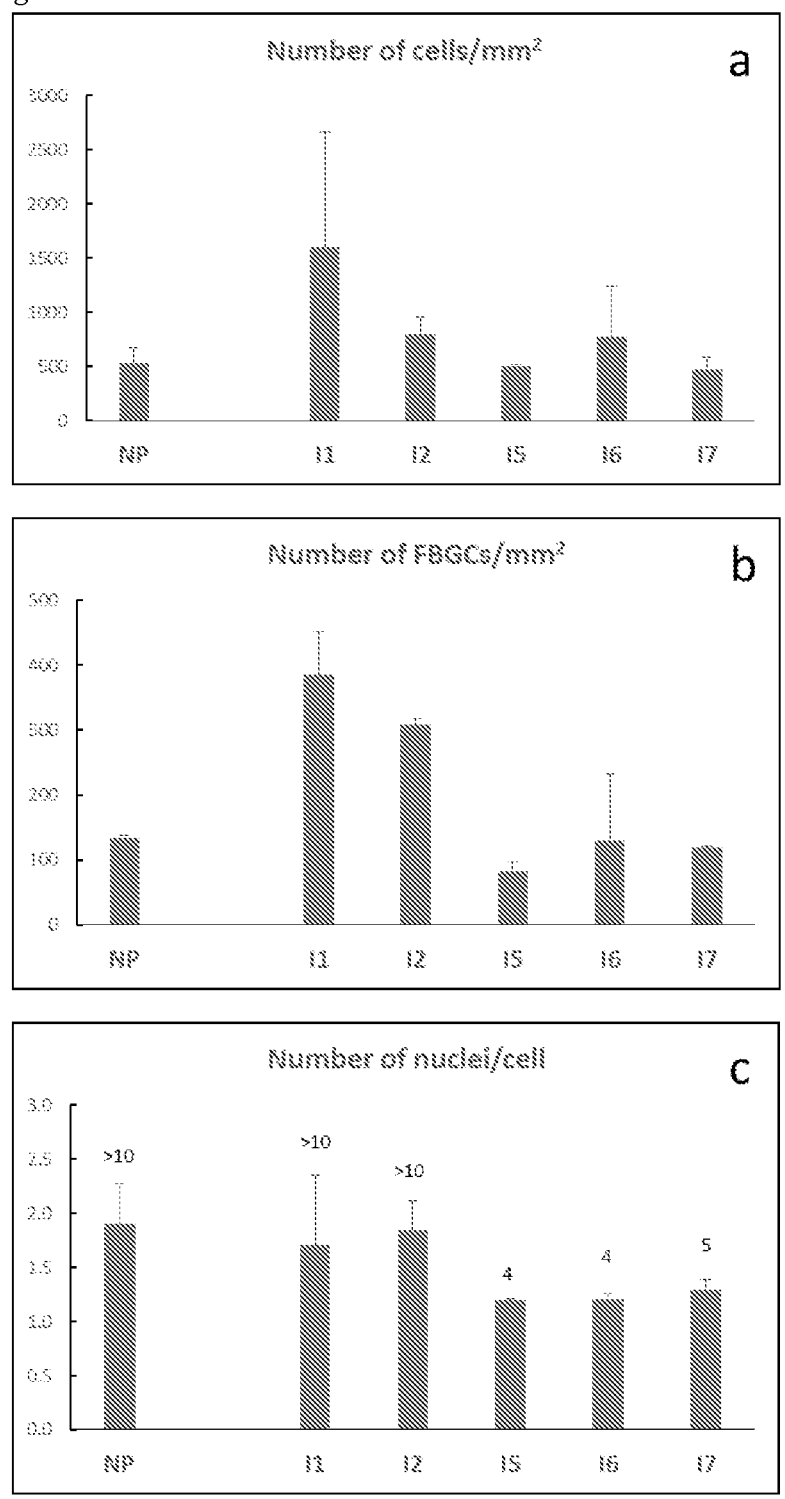
FIG. 10. Topographies I1, I2, I5, I6 and I7 affect the immunoregulation in vitro. Analyzed for (a) total number of cells (mononuclear and multinuclear cells) per mm$^2$, (b) total number of foreign body giant cells (multinuclear cells) per mm$^2$ and (c) average number of nuclei per cell, with numbers presented above each bar indicating the maximum number of nuclei in one cell. The nonpatterned sample (NP) was included as control. Conditions: 10 days of culture, starting with monocyte isolate.

Secondary validation reveals the topographies strongly affect macrophage attachment and FBGC formation in the early stages in vitro (FIG. 10). Difference between macrophage attachments on low vs. high attachment topographies was up to 5 fold, and up to 1.5 fold comparing the low-attachment topographies to the NP surface. FBGC formation on the low vs. high attachment topographies is even stronger reduced, on some topographies even more than decimated, whereas up to 2 fold comparing low-attachment topographies to the NP surfaces. This effect can also be appreciated in the average number of nuclei per cell which is significantly higher on the high vs. low attachment topographies. Comparing the NP surface to the surfaces featuring low-attachment topographies it stands out that besides affecting macrophage attachment itself, FBGC formation and the number of cells that fuse together into one big cell is significantly lowered.

Conclusion

The identified topographies are highly successful in steering early stage immunoregulation through macrophage attachment and their fusion into FBGCs under in vitro conditions. The surface topographies that stimulate high attachment of macrophages and/or FBGC formation in the early stages in vitro are split into two groups regarding their end stage effect: I2 and I4 stimulate the end stage immune response and this group has protrusions with a top surface area of 20-70 µm², surface coverage of 15-25% and average distance between protrusions of 5-12 µm; I1 and I3 reduce the end stage immune response and this group has protrusions with a top surface area of 25-65 µm², surface coverage of 5-10% and average distance between protrusions of 12.1-20 µm. On the other hand, the surface topographies that induce low attachment of macrophages and FBGC formation in the early stages in vitro (I5-I13) and reduce the end stage immune response have protrusions with a top surface area of 25-200 µm², surface coverage of 26-50% and average distance between protrusions of 2-12 µm. All three groups of topographies are capable of affecting immunoregulation, both early stage and late stage, and can be used depending on the final application where either the immune response should be downregulated or stimulated.

Example #7: Surface Topographies to Regulate the Immune Response, In Vivo

To assess the in vivo effectiveness of the surface topographies selected to regulate the immune response, implants featuring these topographies were placed in a subcutaneous mouse model.

Results

Figure 11:
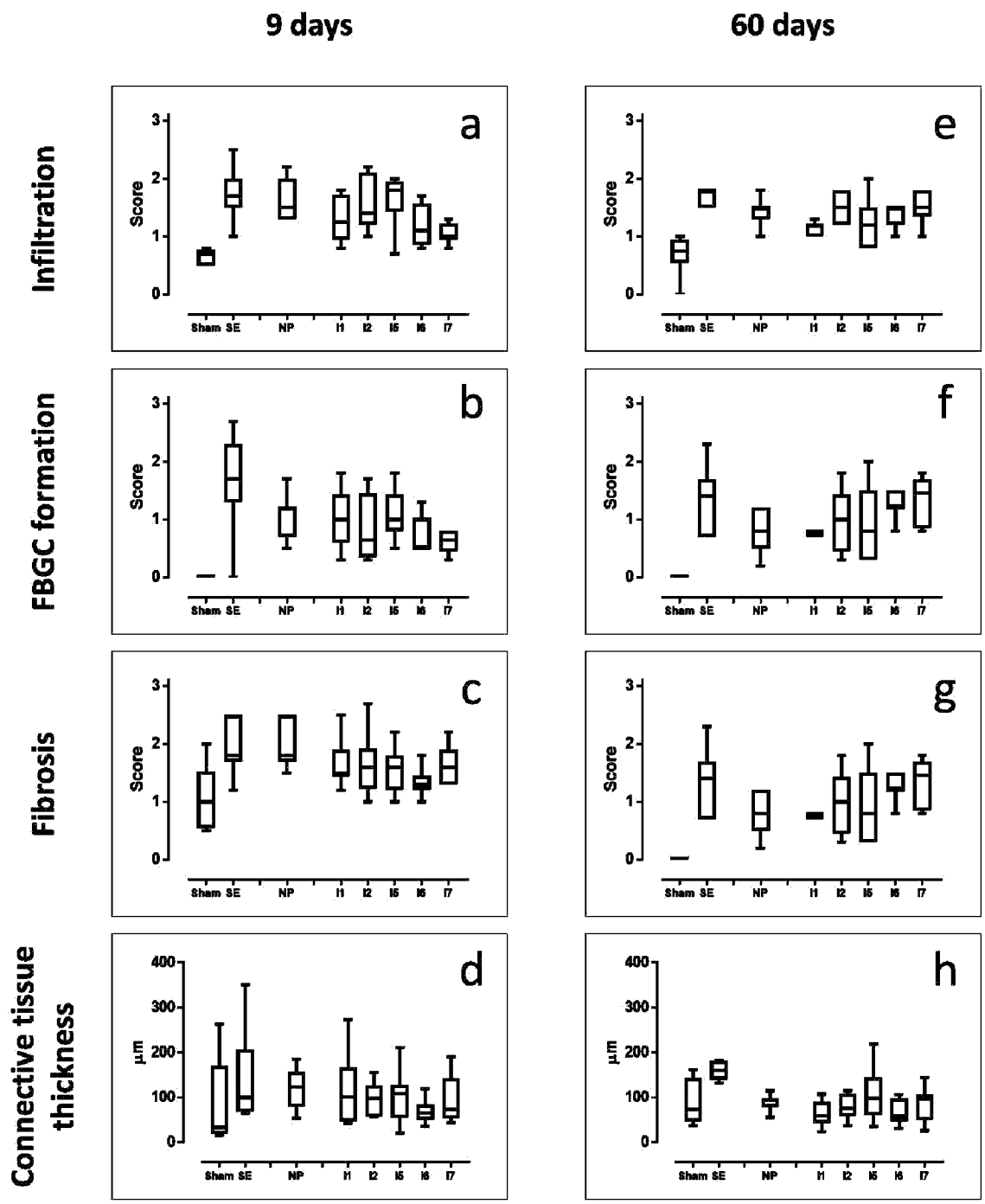
FIG. 11. Topographies I1, I2, I5, I6 and I7 affect the immunoregulation in vivo. Analyzed for (a, e) infiltration of immune cells, (b, f) FBGC formation, (c, g) fibrosis and (d, h) fibrotic capsule thickness at (a-d) 9 and (e-h) 60 days. Conditions: subcutaneous implantation in mice, including NP (control), silicon elastomer (SE, reference material) and empty wound (Sham). The bars present the 25th-75th percentile levels, the line in the middle the median; and the 'error bars' the lowest and highest levels measured.
Figure 12:
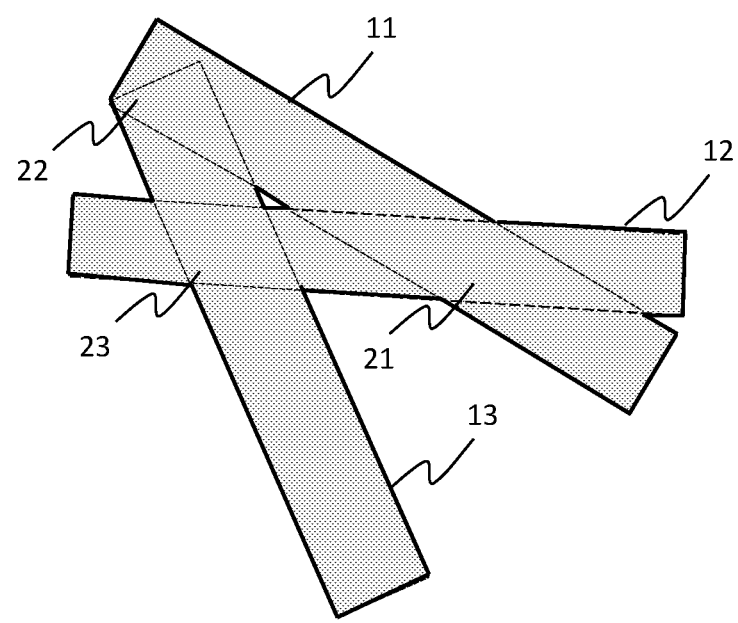
FIG. 12 is schematic top view of a representative protrusion (or protrusion element) having a complex shape comprising a combination of basic shapes 11, 12 and 13 (rectangles) with overlapping portions 21, 22 and 23 between adjacent ones of the basic shapes 11, 12 and 13. The protrusion has shape 19 in FIG. 13.

The surface topographies substantially influenced on the mice' immune system response at both time points (FIG. 11) compared to the controls.

The Sham condition (where no foreign material is implanted, the response is only to the procedure itself) generally has, as expected, the mildest immune response compared to all other conditions at both the early stage (9$d$) and late stage (60$d$) time points. The SE reference material shows a more intense immune response compared the other implanted samples: at 9 days mostly already on the high end compared to the other implants but especially at 60 days there is more immune response activity and fibrosis resulting in the formation of a much thicker layer of connective tissue around the implants. This result is to be expected as the silicon elastomer was included because of its well-known 'normal' inflammatory response. The immune response to the nonpatterned PU implants, a material designed for chronic implantation and good biocompatibility, is initially (9$d$) more moderate to intense and results in moderate immune activity and fibrous capsule formation. Although in general lower than the SE reference material, the response to the NP implants in the course of time is most similar to the response to the SE control group.

The immune response to the PU implants featuring surface topography I1 (type H/L) starts as a moderate response, slightly reduced compared to NP, however at 60 days the immune response is very mild. The early stage in vivo outcome is in line with the relatively high macrophage attachment and FBGC formation in the early stage in vitro model (example 6). The phenomenon of this topography showing one of lowest immune activity levels in the end stage is very interesting and, although not yet fully understood, hypothesized to be due to the initial acute response being appropriate and controlled. The FBGC formation and fibrosis on this topography at the end stage is very consequent (very little variation) and mild, as in the low immune activity and formation of a thin fibrous capsule.

Topography I2 (type H/H) induced a moderate to severe immune response at both time points, at the early stages comparable to I1 but remains at this level in time. Topography I5 (type L/L) also has a moderate to severe immune response at the early stage and becomes rather mild in the late stages but the capsule thickness is higher compared to the other topographies.

Topography I6 (type L/L) shows the mildest FBR compared to biomaterials with surface topographies, NP and SE group. This response, which is the closest to the sham group, starts as a mild to moderate response at and continues that way in the later stages leading to the thinnest fibrous capsule. Topography I7 (type L/L) first shows a similar mild to moderate FBR at 9 days, however at the later time point the FBR is more moderate.

Comparing all implants based on the formed connective tissue, initially (9d) topographies I6 and I7 induce the thinnest fibrous capsule, which is in line with the early stage in vitro results presented in example #6. At the end-stage of the FBR, surface topographies I1 and I6 induce the lowest amount of fibrotic encapsulation compared to the other surface topographies and NP control, even lower than the sham control.

Conclusion

Surface topographies are capable of regulating the foreign body (immune) response in both early (acute) and late (chronic) stages. The FBR to the topography-featuring implants varies from very mild to severe and affects the inflammatory response as well as the fibrous capsule formation and its thickness. Surface topographies of the invention allow for a low early stage and a low late stage immune response, leading to reduced fibrotic encapsulation at late stage FBR (2 months), and these surfaces had protrusions with a top surface area of 25-200 $\mu m^2$, surface coverage of 26-50% and average distance between protrusions of 2-12 $\mu m$. In addition, surface topographies of the invention allow for a high early stage and a high late stage immune response, leading to stimulation of controlled fibrotic encapsulation at late stage FBR (2 months), and these surfaces had protrusions with a top surface area of 20-70 $\mu m^2$, surface coverage of 15-25% and average distance between protrusions of 5-12 $\mu m$. In addition, surface topographies of the invention allow for a high early stage and a low late stage immune response, leading to reduced fibrotic encapsulation at late stage FBR (2 months), and these surfaces had protrusions with a top surface area of 25-65 $\mu m^2$, surface coverage of 5-10% and average distance between protrusions of 12.1-20 $\mu m$.

The invention claimed is:

1. An object implantable in a body, the object comprising:
    a surface part provided with at least one topography capable of modulating morphology, proliferation, biochemical functioning, differentiation, attachment, migration, signaling, and/or cell death of a cell population by physical stimulation,
    wherein the at least one topography comprises a surface and a plurality of protrusions protruding from the surface, wherein the plurality of protrusions are individually spaced and arranged in a regular pattern,
    wherein the plurality of protrusions define a plurality of valleys between adjacent protrusions of the plurality of protrusions, such that the adjacent protrusions do not touch;
    wherein each protrusion of the plurality of protrusions comprises at least one protrusion element, wherein the at least one protrusion element comprises a surface portion which is elevated above the surface and which has a top surface area and a circumferential side face connecting the top surface area with the surface,
    wherein the at least one protrusion element of each protrusion has a maximum height of between 0.5 and 50 $\mu m$ above the surface,
    wherein an average distance between the adjacent protrusions is between 0.5 and 50 $\mu m$,
    wherein the top surface area of the at least one protrusion element of each protrusion is between 1 and 6000 $\mu m^2$,
    wherein the plurality of protrusions cover between 3 and 90% of the surface, and
    wherein the top surface area of the at least one protrusion element of each protrusion has a complex shape comprising a combination of basic shapes, interconnected by one or more overlapping portions, the basic shapes comprising one or more of a circular, oval, triangular, square, rectangular, trapezoidal, pentagonal, hexagonal, heptagonal or octagonal shape.

2. The object of claim 1, wherein the surface part is formed from a material selected from a group consisting of a metal, polymeric, composite or ceramic material.

3. The object of claim 1, wherein the regular pattern of the plurality of protrusions is defined by a grid of intersecting gridlines laid over the surface, wherein the intersecting gridlines define unit cells, such that each unit cell comprises a maximum of one protrusion.

4. The object of claim 1, wherein the surface part is provided with no more than 10 different topographies.

5. The object of claim 4, wherein the at least one topography is configured for modulating the morphology, proliferation, biochemical functioning, differentiation, attachment, migration, signaling, and/or cell death of a cell population by physical stimulation in vitro.

6. The object of claim 5, wherein the modulation comprises maintaining hepatocyte phenotype and functioning, wherein the at least one topography is defined by:
    the average distance between adjacent protrusions is between 3-25 $\mu m$;
    the top surface area of the at least one protrusion element is between 20-250 $\mu m^2$; and
    the plurality of protrusions cover 8-35% of the surface part.

7. The object of claim 1, wherein the at least one topography is defined by:
    the average distance between the adjacent protrusions is 2-25 $\mu m$;
    the top surface area of the at least one protrusion element is between 30 and 750 $\mu m^2$; and
    the plurality of protrusions cover between 30 and 65% of the surface.

8. The object of claim 1, wherein the at least one topography is defined by:
    the average distance between the adjacent protrusions is 3-25 $\mu m$;
    the top surface area of the at least one protrusion element is between 20 and 250 $\mu m^2$; and
    the plurality of protrusions cover between 8 and 35% of the surface.

9. The object of claim 1, wherein the at least one topography is configured to regulate an immune response to a foreign body by suppressing the immune response, wherein the at least one topography is defined by:
    the average distance between the adjacent protrusions is 2-12 $\mu m$;
    the top surface area of the at least one protrusion element is between 20 and 200 $\mu m^2$; and
    the plurality of protrusions cover between 26 and 50% of the surface.

10. The object of claim 1, wherein the at least one topography is configured to regulate an immune response to a foreign body by stimulating the immune response, wherein the at least one topography is defined by:

the average distance between the adjacent protrusions is 5-12 µm;

the top surface area of the at least one protrusion element is between 20 and 70 µm$^2$; and the plurality of protrusions cover between 15 and 25% of the surface.

11. The object of claim 1, wherein the at least one topography is configured to regulate an immune response to a foreign body by stimulating an early stage of the immune response to the foreign body to result in a lowered end stage immune response, wherein the at least one topography is defined by:

the average distance between the adjacent protrusions is 12.1-20 µm;

the top surface area of the protrusion is between 25 and 65 µm$^2$; and the protrusions cover between 5 and 10% of the surface.

12. The object of claim 1, wherein:

at least one protrusion comprises one protrusion element;

the height of the protrusion element is defined as the length of the longest straight-line fitting within the circumference of the top surface area parallel to the surface; and a width of the protrusion element is defined as the length of the longest straight-line fitting within the circumference of the top surface area parallel to the surface, perpendicular to the length, and is 0.01-100 µm.

13. The object of claim 1, wherein:

at least one protrusion comprises more than one protrusion element;

the height of each protrusion element is defined as the length of the longest straight-line fitting within the circumference of the top surface area parallel to the surface;

a width of each protrusion element is defined as the length of the longest straight-line fitting within the circumference of the top surface area parallel to the surface perpendicular to the length, and is 0.01-100 µm; and an average distance between two circumferences of adjacent protrusion elements of the same protrusion is 0.5-50 µm.

14. The object of claim 1, wherein at least a portion of each protrusion of the plurality of protrusions extends substantially normal to the surface where the circumferential side face intersects with the surface.

15. The object of claim 14, wherein the at least the portion of each protrusion of the plurality of protrusions extends substantially normal to the surface at an angle in a range of about 88° to about 92°.

16. A method for modulating morphology, proliferation, biochemical functioning, differentiation, attachment, migration, signaling, and/or cell death of a cell population, comprising one or more cells, by physical stimulation, the method comprising:

contacting the one or more cells in a suitable medium with a surface part of an object which is provided with a plurality of individually spaced protrusions protruding from the surface part and defining a plurality of valleys between adjacent protrusions of the plurality of protrusions, such that the adjacent protrusions do not touch, wherein the plurality of protrusions are arranged in a regular pattern, defined by a grid of intersecting gridlines which laid over the surface part, wherein the gridlines define a pattern of unit cells, such that each unit cell comprises a maximum of one protrusion, wherein each protrusion of the plurality of protrusions comprises at least one protrusion element, wherein the at least one protrusion element comprises a surface portion which is elevated above the surface and which has a top surface area and a circumferential side face connecting the top surface area with the surface, wherein the at least one protrusion element of each protrusion has a maximum height of between 0.5 and 50 µm above the surface, wherein an average distance between the adjacent protrusions is between 0.5 and 50 µm, wherein the top surface area of the at least one protrusion element of each protrusion is between 1 and 6000 µm$^2$, wherein the plurality of protrusions cover between 3 and 90% of the surface, and wherein the top surface area of the at least one protrusion element of each protrusion is a complex shape comprising a combination of basic shapes, interconnected by one or more overlapping portions, the basic shapes comprising one or more of a circular, oval, triangular, square, rectangular, trapezoidal, pentagonal, hexagonal, heptagonal or octagonal shape; and allowing the cells to respond to the surface.

17. The method of claim 16, wherein the one or more cells are hepatocytes, and wherein:

the average distance between the adjacent protrusions is between 3-25 µm;

the top surface area of the at least one protrusion element is between 20-250 µm$^2$; and the plurality of protrusions cover 8-35% of the surface part.

* * * * *